(12) United States Patent
Dirlam et al.

(10) Patent No.: US 6,472,371 B1
(45) Date of Patent: Oct. 29, 2002

(54) MACROLIDES

(75) Inventors: John Philip Dirlam, Gales Ferry; Hamish Alastair Irvine McArthur, Mystic; Alan Elwood Blize, New London, all of CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/554,988

(22) PCT Filed: Dec. 21, 1998

(86) PCT No.: PCT/IB98/02099

§ 371 (c)(1),
(2), (4) Date: May 23, 2000

(87) PCT Pub. No.: WO99/35156

PCT Pub. Date: Jul. 15, 1999

Related U.S. Application Data

(60) Provisional application No. 60/070,343, filed on Jan. 2, 1998.

(51) Int. Cl.[7] .................. A01N 43/04; A61K 31/70; C07H 17/08; C07H 1/00; C07G 17/00
(52) U.S. Cl. .................. 514/29; 536/7.2; 536/7.4; 536/124
(58) Field of Search .................. 514/29; 536/7.4, 536/7.2, 124

(56) References Cited

U.S. PATENT DOCUMENTS 5,332,807 A * 7/1994 Waddell et al. .............. 536/7.4
5,441,939 A * 8/1995 Yang .............................. 514/29

FOREIGN PATENT DOCUMENTS

| EP | 0283055 A | * | 9/1988 | ......... C07D/267/00 |
| EP | 0 619320 A1 | * | 10/1994 | ........... C07H/17/08 |
| FR | 2 691464 | * | 11/1993 | ........... C07H/17/08 |

OTHER PUBLICATIONS

Djokic et al. ("Erythromycin series. part 11. Ring Expansion of erythromycin A oxime by the Beckmann rearrangement", J. Chem. Soc. Perkin Trans. 1 (1986), 11, 1881–09.*

Djokic et al. (Erythromycin series. part 13. Synthesis and structure elucidation of 10–dihydro–10–deoxo–11–methyl–11–azaerythromycin A).*

* cited by examiner

*Primary Examiner*—Ethan C. Whisenant
(74) *Attorney, Agent, or Firm*—Peter C. Richardson; Gregg C. Benson; Lorraine Ling

(57) ABSTRACT

The invention relates to novel erythromycin analogs and azalides, particularly ones with novel C-13 substituents, and to pharmaceutically acceptable salts thereof. The compounds of this invention are antibacterial agents that may be used to treat various bacterial and protozoa infections. The invention also relates to pharmaceutical compositions containing such compounds and to methods of treating bacterial protozoa infections by administering such compounds. The invention also relates to methods of preparing such compounds and to intermediates useful in such preparation.

9 Claims, No Drawings

MACROLIDES

This application is the U.S. national phase of PCT/IB98/02099 filed Dec. 23, 1998 which claims benefit to U.S. provisional application No. 60/070,343 filed Jan. 2, 1998.

BACKGROUND OF THE INVENTION

This invention relates to novel erythromycins and azalides that are useful as antibacterial agents and antiprotozoa agents and other applications (e.g., anticancer, atherosclerosis, gastric motility reduction, etc.) in mammals, including man, as well as in fish and birds. This invention also relates to pharmaceutical compositions containing the novel compounds and to methods of treating bacterial infections and protozoa infections and in mammals, fish and birds by administering the novel compounds to mammals, fish and birds requiring such treatment Macrolide antibiotics are known to be useful In the treatment of a broad sprectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Additional macrolides are referred to in U.S. patent application serial No. 60/063676, filed Oct. 29, 1997 (Yong-Jin Wu), U.S. application serial No. 60/053161, filed Oct. 29, 1997 (Yong-Jin Wu), U.S. application serial No. 60/054866, filed Aug. 6, 1997 (Hiroko Masamune, Yong-Jin Wu, Takushi Kaneko and Paul R. McGuirk), U.S. application serial No. 60/049980, filed Jun. 11, 1997 (Brian S. Bronk, Michael A. Latavik, Takushi Kaneko and Bingwel V. Yang), U.S. application serial No. 60/049348, filed Jun. 11, 1997 (Brian S. Bronk, Hengmiao Cheng, E. A. Glaser, Michael A, Letavic, Takushi Kaneko and Bingwei V. Yang), International Application No. PCT/GB97/01810 filed Jul. 4, 1997 (Peter Francis Leadlay, James Staunton, Jesus Cortes and Michael Stephen Pacey), International Application No. PCT/GB97/01819 filed Jul. 4, 1997 (Peter Francis Leadlay, James Staunton, and Jesus Cortes), U.S. application serial No. 60/070343, filed Jan. 2, 1998, (Diriam), U.S. application serial No. 60/070358, filed Jan. 2, 1998 (Yong-Jin Wu) and U.S. application serial No. 60/097075, filed Aug. 19, 1998 (Hengmiao Cheng, Michael A Letavic, Carl B. Ziegler, Jason K, Dutra, Brian S. Bronk), all of which are incorporated herein by reference in their entirety. Like azithromycin and other macrolide antibiotics, the novel macrolide compounds of the present invention possess potent activity against various bacterial infections and protozoa infections as described below.

SUMMARY OF THE INVENTION

The present invention relates to compounds of the formula

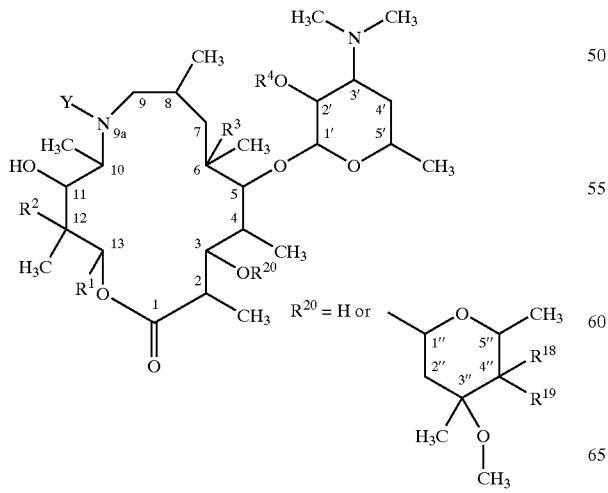

or a pharmaceutically acceptable salt thereof, wherein:

Y is H, $C_1$–$C_{10}$ alkyl, $C_{2-10}$ alkenyl, $C_2$–$C_{10}$ alkynyl, —$(CH_2)_m C_8$–$C_{10}$aryl, —$(CH_2)_m$(5–10 membered heteroaryl), wherein m is an integer ranging from 0 to 4, and wherein the alkyl, alkenyl, aryl, heteroaryl and alkynyl groups are optionally substituted by 1 to 3 substituents independently selected from halo, cyano, nitro, trifluoromethyl, azido, —$C(O)R^{21}$, —$OC(O)R^{21}$, —$NR^{21}C(O)R^{22}$, —$C(O)NR^{21}R^{22}$, —$NR^{21}R^{22}$, hydroxy, $C_1$–$C_6$ alkyl, $C_1$–$C_8$ alkoxy, $C_6$–$C_{10}$ aryl, and 5–10 membered heteroaryl;

$R^1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms: or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ may be with a formula (a) as shown below:

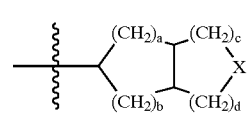

wherein X is O, S or —$CH_2$—, a, b, c, and d are each independently an integer ranging from 0 to 2 and a+b+c+d≦5;

or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$–$C_8$cycloalkyl or $C_5$–$C_8$cyloalkenyl either or which may be optionally substituted by methyl or one or more $C_1$–$C_4$alkyl groups or halo atoms; or a 3 to 6 membered oxygen or sulphur containing heterocyclic ring which may be saturated or fully or partially unsaturated and which may optionally be substituted by one or more $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one or more $C_1$–$C_4$ alkyl groups or halo atoms;

$R^2$ is H or OH;

$R^3$ is H, OH, or $OCH_3$;

$R^4$ is H, —$C(O)R^9$, —$C(O)OR^9$, —$C(O)NR^9R^{10}$ or a hydroxy protecting group;

$R^5$ is —$SR^8$, —$(CH_2)_nC(O)R^8$ wherein n is 0 or 1, $C_1$–$C_{10}$ alkyl, $C_2$–$C_{10}$ alkenyl, $C_2$–$C_{10}$ alkynyl, —$(CH_2)_m$ ($C_6$–$C_{10}$ aryl), or —$(CH_2)_m$(5–10 membered heteroaryl), wherein m is an integer ranging from 0 to 4, and wherein the foregoing $R^5$ groups are optionally substituted by 1 to 3 $R^{16}$ groups;

each $R^6$ and $R^7$ is independently H, hydroxy, $C_1$–$C_6$ alkoxy, $C_1$–$C_6$ alkyl, $C_2$–$C_6$ alkenyl, $C_2$–$C_6$ alkynyl, —$(CH_2)_m(C_6$–$C_{10}$ aryl), or —$(CH_2)_m$(5–10 membered heteroaryl), wherein m is an integer ranging from 0 to 4;

each $R^8$ is independently H, $C_1$–$C_{10}$ alkyl, $C_2$–$C_{10}$ alkenyl, $C_2$–$C_{10}$ alkynyl, —$(CH_2)_qCR^{11}R^{12}(CH_2)_r$ $NR^{13}R^{14}$ wherein q and r are each independently an integer ranging from 0 to 3 except q and r are not both 0, —$(CH_2)_m(C_6$–$C_{10}$ aryl), or —$(CH_2)_m$(5–10 membered heteroaryl), wherein m is an integer ranging from 0 to 4, and wherein the foregoing $R^8$ groups except H, are optionally substituted by 1 to 3 $R^{16}$ groups;

or where $R^8$ is as —$CH_2NR^8R^{15}$, $R^{15}$ and $R^8$ may be taken together to form a 4–10 membered monocyclic or polycyclic saturated ring or a 5–10 membered heteroaryl ring, wherein said saturated and heteroaryl rings optionally include 1 or 2 heteroatoms selected from O, S and —$N(R^8)$—, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{15}$ groups;

each $R^9$ and $R^{10}$ is independently H or $C_1$–$C_6$ alkyl;

each $R^{11}$, $R^{12}$, $R^{13}$ and $R^{14}$ is independently selected from H, $C_1$–$C_{10}$ alkyl, —$(CH_2)_m(C_5$–$C_{10}$ aryl), and —$(CH_2)_m$ (5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —$(CH_2)_p$— wherein p is an integer ranging from 0 to 3 such that a 4–7 membered saturated ring is formed that optionally includes 1 or 2 carbon-carbon double or triple bonds;

or $R^{13}$ and $R^{14}$ are taken together to form a 4–10 membered monocyclic or polycyclic saturated ring or a 6–10 membered heteroaryl ring, wherein said saturated and heteroaryl rings optionally include 1 or 2 heteroatoms selected from O, S and —$N(R^8)$—, in addition to the nitrogen to which $R^{13}$ and $R^{14}$ are attached, said saturated ring optionally includes 1 or 2 carbon-carbon double or triple bonds, and said saturated and heteroaryl rings are optionally substituted by 1 to 3 $R^{16}$ groups;

$R^{15}$ is H, $C_1$–$C_{10}$ alkyl, $C_2$–$C_{10}$ alkenyl, or $C_2$–$C_{10}$ alkynyl, wherein the foregoing $R^{15}$ groups are optionally substituted by 1 to 3 substituents independently selected from halo and —$OR^9$;

each $R^{16}$ is independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)$ $NR^6R^7$, —$NR^6R^7$, hydroxy, $C_1$–$C_6$ alkyl, $C_1$–$C_8$ alkoxy, —$(CH_2)_m(C_6$–$C_{10}$ aryl), and —$(CH_2)_m$(5–10 membered heteroaryl), wherein m is an integer ranging from 0 to 4, and wherein said aryl and heteroaryl subsituents are optionally substituted by 1 or 2 substituents independently selected from halo, cyano, nitro, trifluoromethyl, azido, —$C(O)R^{17}$, —$C(O)OR^{17}$, —$C(O)OR^{17}$, —$OC(O)OR^7$, —$NR^6C(O)R^7$, —$C(O)$ $NR^6R^7$, —$NR^6R^7$, hydroxy, $C_1$–$C_6$ alkyl, and $C_1$–$C_6$ alkoxy;

each $R^{17}$ is independently selected from H, $C_1$–$C_{10}$ alkyl, $C_2$–$C_1$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4, provided that $R^8$ is not H where $R^{19}$ is —$CH_2S(O)_nR^8$;

$R^{18}$ is OH;

$R^{19}$ is $C_1$–$C_{10}$, alkyl, $C_2$–$C_{10}$ alkenyl, $C_2$–$C_{10}$ alkynyl, cyano, —$CH_2S(O)_nR^8$ wherein n is an integer ranging from 0 to 2, —$CH_2OR^8$, —$CH_2N(OR^9)R^8$, —$CH_2NR^8R^{15}$, —$(CH_2)_m(C_6$–$C_{10}$ aryl), or —$(CH_2)_m$ (5–10 membered heteroaryl), wherein m is an integer ranging from 0 to 4, and wherein the foregoing $R^{19}$ groups are optionally substituted by 1 to 3 $R^{16}$ groups;

or $R^{18}$ and $R^{19}$ are taken together to form an oxazolyl ring as shown below

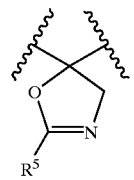

and;

each $R^{21}$ and $R^{22}$ is independently H, hydroxy, $C_1$–$C_6$ alkoxy, $C_1$–$C_6$ alkyl, $C_2$–$C_8$ alkenyl, $(CH_2)_m(C_6$–$C_{10})$ aryl, $(CH_2)_m$(5–10 membered heteroaryl), wherein m is an integer ranging from 0 to 4, or $C_2$–$C_{10}$ alkylyl.

The present invention further relates to compounds of the formula

II

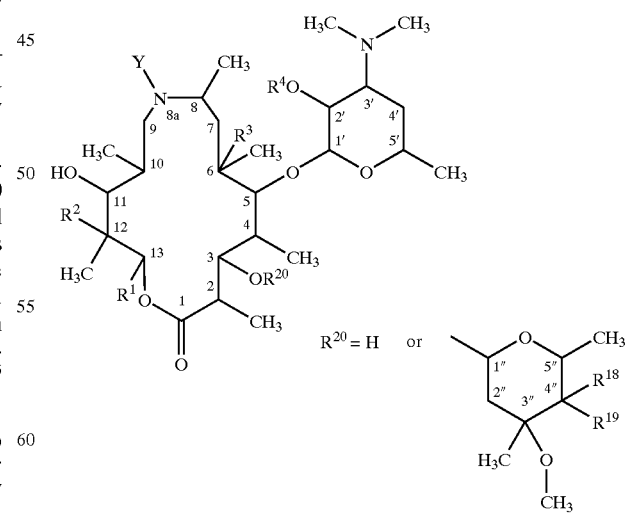

or a pharmaceutically acceptable salt thereof, wherein:

Y is H, $C_1$–$C_{10}$ alkyl, $C_2$–$C_{10}$ alkenyl, $C_2$–$C_{10}$ alkynyl, —$(CH_2)_mC_6$–$C_{10}$aryl, —$(CH_2)_m$(5–10 membered heteroaryl), wherein m is an integer ranging from 0 to 4, and wherein the alkyl, alkenyl, aryl, heteroaryl and alkynyl groups are optionally substituted by 1 to 3 substituents independently selected from halo, cyano, nitro, trifluoromethyl, azido, —C(O)R$^{21}$, —OC(O)R$^{21}$, —NR$^{21}$C(O)R$^{22}$, —C(O)NR$^{21}$R$^{22}$, —NR$^{21}$R$^{22}$, hydroxy, C$_1$–C$_6$ alkyl, C$_1$–C$_6$ alkoxy, C$_6$–C$_{10}$ aryl, and 5–10 membered heteroaryl;

R$^1$ is an alpha-branched C$_3$–C$_8$ alkyl, alkenyl, alkynyl, alkoxyalkyl or alkylthioalkyl group any of which may optionally be substituted by one or more hydroxyl groups; a C$_5$–C$_8$ cycloalkylalkyl group wherein the alkyl group is an alpha-branched C$_2$–C$_5$ alkyl group; a C$_3$–C$_8$ cycloalkyl or C$_5$–C$_8$ cycloalkenyl group, either of which may optionally be substituted by methyl or one or more hydroxyl or one or more C$_1$–C$_4$ alkyl groups or halo atoms; or a 3 to 6 membered oxygen or sulphur containing heterocyclic ring which may be saturated, or fully or partially unsaturated and which may optionally be substituted by one or more C$_1$–C$_4$ alkyl groups or halo atoms;

or R$^1$ is phenyl which may be optionally substituted with at least one substituent selected from C$_1$–C$_4$ alkyl, C$_1$—C$_4$ alkoxy and C$_1$–C$_4$ alkylthio groups, halogen atoms, hydroxyl groups, trifluoromethyl, and cyano; or R$^1$ may be with a formula (a) as shown below:

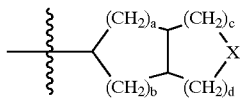

a wherein X is O, S or —CH$_2$—, a, b, c, and d are each independently 0–2 and a+b+c+d≦5;

or R$^1$ is CH$_2$R$^{24}$, wherein R$^{24}$ is H, C$_1$–C$_8$alkyl, C$_2$–C$_8$alkenyl, C$_2$–C$_8$alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a C$_3$–C$_8$cycloalkyl or C$_5$–C$_8$cycloalkenyl either or which may be optionally substituted by methyl or one or more C$_1$–C$_4$alkyl groups or halo atoms; or a 3 to 6 membered oxygen or sulphur containing heterocyclic ring which may be saturated or fully or partially unsaturated and which may optionally be substituted by one or more C$_1$–C$_4$alkyl groups or halo atoms: or a group of the formula SR$^{23}$ wherein R$^{23}$ is C$_1$–C$_8$alkyl, C$_2$–C$_8$alkenyl, C$_2$–C$_8$alkynyl, C$_3$–C$_8$cycloalkyl, C$_5$–C$_8$cycloalkenyl, phenyl or substituted phenyl wherein the substituent is C$_1$–C$_4$alkyl, C$_1$–C$_4$alkoxy or halo, or a 3 to 6 membered oxygen or sulphur-containing heterocyclic ring which may be saturated, or fully or partially unsaturated and which may optionally be substituted by one or more C$_1$–C$_4$alkyl groups or halo atoms;

R$^2$ is H or OH;

R$^3$ is H, OH, or OCH$_3$;

R$^4$ is H, —C(O)R$^9$, —C(O)OR$^9$, —C(O)NR$^9$R$^{10}$ or a hydroxy protecting group;

each R$^9$ and R$^{10}$ is independently H or C$_1$–C$_6$ alkyl;

R$^{18}$ is OH;

R$^{10}$ is H and;

each R$^{21}$ and R$^{22}$ is independently H, hydroxy, C$_1$–C$_6$ alkoxy, C$_1$–C$_6$ alkyl, C$_2$–C$_6$ alkenyl, (CH$_2$)$_m$(C$_6$–C$_{10}$) aryl, (CH$_2$)$_m$(5–10 membered heteroaryl), wherein m is an integer ranging from 0 to 4, or C$_2$–C$_{10}$ alkylyl.

The compounds of formula I are exemplified by the compounds of formulas 5 and 6, described below, wherein Y=H and CH$_3$, respectively.

Preferred compounds of formula I include those wherein R$^1$=isopropyl, sec-butyl, cyclopropyl, cyclobutyl, cyclopentyl, methylthioethyl and 3furyl.

The compounds of formula II are exemplified by the compounds of formulas 6 and 6a described below, wherein Y=H and CH$_3$, respectively.

Preferred compounds of formula II include those wherein R$^1$=isopropyl, sec-butyl, cyclopropyl, cyclobutyl, cyclopentyl, methylthioethyl and 3-furyl.

Other preferred compounds of formula I and formula II include those wherein R$^{20}$ is

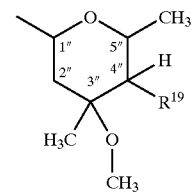

and

R$^1$ is isopropyl, R$^2$ is H and R$^{19}$ is OH;

R$^1$ is isopropyl, R$^2$ is OH and R$^{19}$ is OH;

R$^1$ is cyclopropyl, R$^2$ is H and R$^{19}$ is OH;

R$^1$ is cyclopropyl, R$^2$ is OH and R$^{19}$ is OH;

R$^1$ is sec-butyl, R$^2$ is H and R$^{19}$ is OH;

R$^1$ is sec-butyl, R$^2$ is OH and R$^{19}$ is OH;

R$^1$ is cyclobutyl, R$^2$ is H and R$^{19}$ is OH;

R$^1$ is cyclobutyl, R$^2$ is OH and R$^{19}$ is OH;

R$^1$ is cyclopentyl, R$^2$ is H and R$^{19}$ is OH;

R$^1$ is cyclopentyl, R$^2$ is OH and R$^{19}$ is OH;

R$^1$ is methylthioethyl, R$^2$ is H and R$^{19}$ is OH;

R$^1$ is methylthioethyl, R$^2$ is OH and R$^{19}$ is OH;

R$^1$ is 3-furyl, R$^2$ is H, R$^{19}$ is OH and or

R$^1$ is 3-furyl, R$^2$ is OH and R$^{19}$ is OH.

The invention further relates to compounds of the 2, 2a, 3, 3a, 4, 5, 6, 7, 8, 9, 10, 11, 12, 13, 14, 15, 16, 17, and 18.

The invention further relates to a compound of the formula

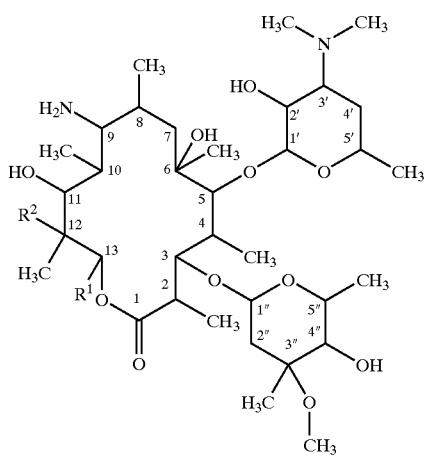

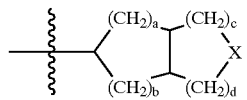

or a pharmaceutically acceptable salt thereof, wherein:

$R^1$ is an alpha-branched $C_3$–$C_8$ alkyl, alkynyl, alkoxyalkyl or alkylthioalkyl group any of which may optionally be substituted by one or more hydroxyl groups; a $C_5$–$C_8$ cylcloalkylalkyl group wherein the alkyl group is an alpha-branched $C_2$–$C_5$ alkyl group; a $C_3$–$C_8$ cycloalkyl or $C_5$–$C_8$ cycloalkenyl group, either of; which may optionally be substituted by methyl or one or more hydroxyl or one or more $C_1$–$C_4$ alkyl groups or halo atoms: or a 3 to 6 membered oxygen or sulphur containing heterocyclic ring which may be saturated, or fully or partially unsaturated and which may optionally be substituted by one or more $C_1$–C4 alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R^1$ may be with a formula (a) as shown below:

wherein X is O, S or —$CH_2$—, a, b, c, and d are each independently 0–2 and $a+b+c+d \leq 5$;

or $R^1$ is $CH_2R^{24}$, wherein $R^{24}$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$–$C_8$ cycloalkyl or $C_5$–$C_8$ cycloalkenyl either or which may be optionally substituted by methyl or one or more $C_1$–$C_4$ alkyl groups or halo atoms; or a 3 to 6 membered oxygen or sulphur containing heterocyclic ring which may be saturated or fully or partially unsaturated and which may optionally be substituted by one or more $C_1$–$C_4$ alkyl groups or halo atoms; or a group of the formula SR23 wherein $R^{23}$ is $C_1$–$C_8$ alkyl, $C_2$–$C_8$ alkenyl, $C_2$–$C_8$ alkynyl, $C_3$–$C_8$ cycloalkyl, $C_5$–$C_8$ cycloalkenyl, phenyl or substituted phenyl wherein the substituent is $C_1$–$C_4$ alkyl, $C_1$–$C_4$ alkoxy or halo, or a 3 to 6 membered oxygen or sulphur-containing heterocyclic ring which may be saturated, or fully or partially unsaturated and which may optionally be substituted by one or more $C_1$-$C_4$ alkyl groups or halo atoms; and $R^2$ is H or OH.

The invention further relates to a compound of the formula

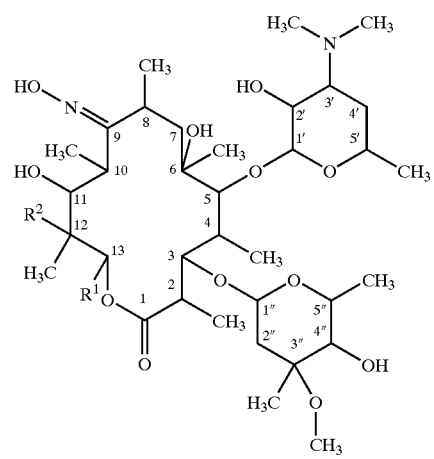

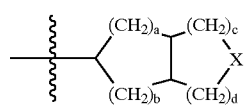

or a pharmaceutically acceptable salt thereof, wherein:

$R^1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alphabranched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano; or $R_1$ may be with a formula (a) as shown below:

wherein X is O, S or —$CH_2$—, a, b, c, and d are each independently 0–2 and $a+b+c+d \leq 6$;

or $R^1$ is $CH_2R^{24}$, wherein $R^{24}$ is H, $C_1$–$C_8$ alkyl, $C_2$–$C_8$ alkenyl, $C_2$–$C_8$ alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms, or a $C_3$–$C_8$cycloalkyl or $C_5$–$C_8$cycloalkenyl either or which may be optionally substituted by methyl or one or more $C_1$–$C_4$alkyl groups or halo atoms; or a 3 to 6 membered oxygen or sulphur containing heterocyclic ring which may be saturated or fully or partially unsaturated and which may optionally be substituted by one or more $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one or more $C_1$–$C_4$alkyl groups or halo atoms; and $R^2$ is H or OH.

The invention also relates to a pharmaceutical composition for the treatment of a bacterial infection or a protozoa infection in a mammal, fish, or bird which comprises a therapeutically effective amount of a compound of formulas I, II, 8, or 9, or a pharmaceutically acceptable salt thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula I, II, 8, or 9, or a pharmaceutically acceptable salt thereof.

The invention also relates to a process for preparing a compound of the formula

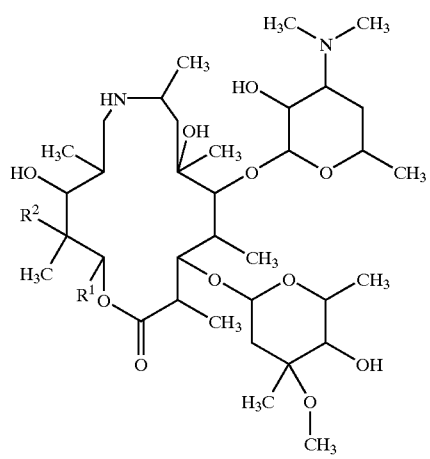

wherein $R^1$ and $R^2$ are as defined for the compound of formula I, which comprises treating a compound of the formula

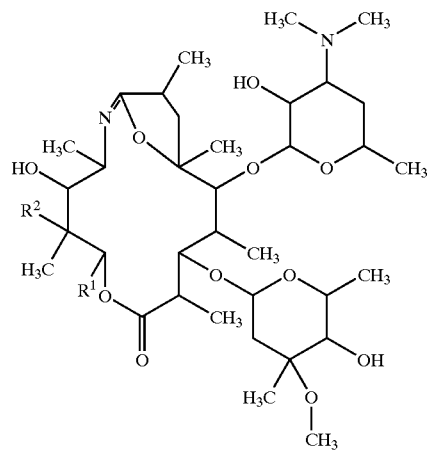

wherein $R^1$ and $R^2$ are as defined for the compound of formula I, with a reducing agent.

The invention also relates to the above process wherein the reducing agent is $NaBH_4$ or platinum oxide.

The invention also relates to a process for preparing a compound of the formula

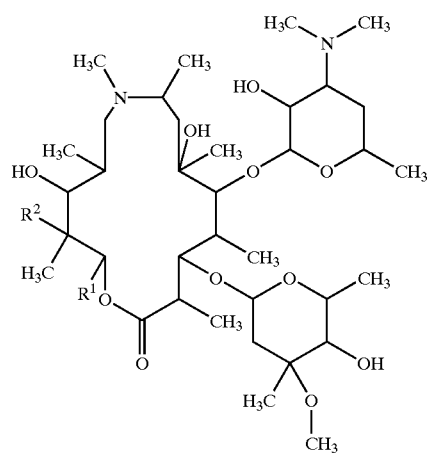

wherein $R^1$ and $R^2$ are as defined for the compound of formula I, which comprises treating a compound of the formula

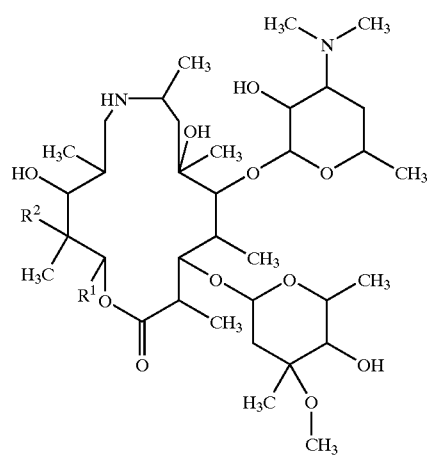

wherein $R^1$ and $R^2$ are as defined for the compound of formula I, with a methylating agent.

The invention also relates to the above process wherein the methylating agent is formaldehyde.

The invention also relates to a process for preparing a compound of the formula

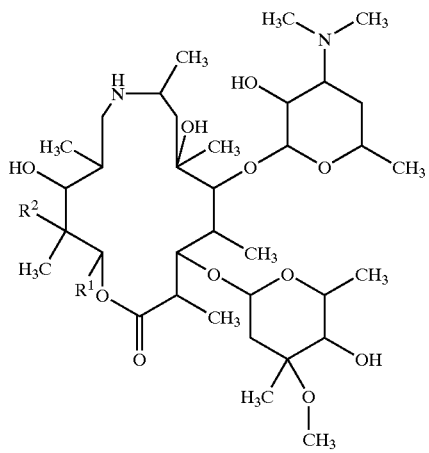

5a wherein $R^1$ and $R^2$ are as defined for the compound of formula I, which comprises treating a compound of the formula

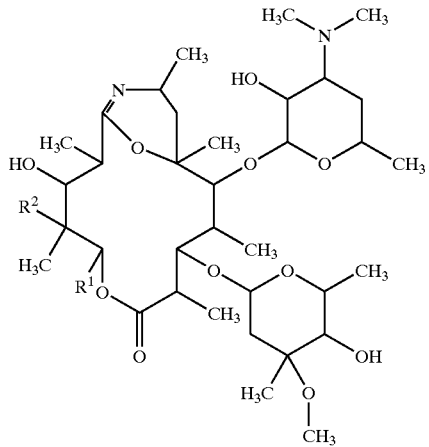

3a wherein $R^1$ and $R^2$ are as defined for the compound of formula I, with a reducing agent.

The invention also relates to the above process wherein the reducing agent is $NaBH_4$ or platinum oxide.

The invention also relates to a process for preparing a compound of the formula

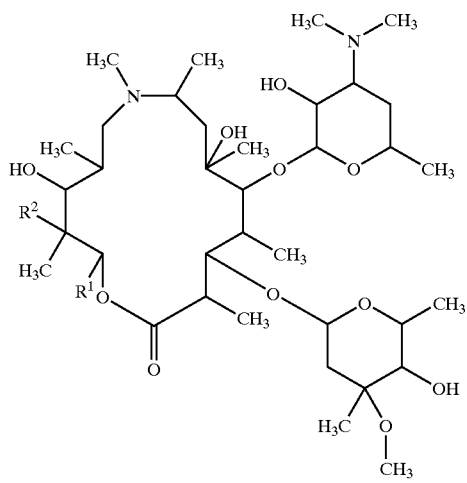

6a wherein $R^1$ and $R^2$ are as defined for the compound of formula I, which comprises treating a compound of the formula

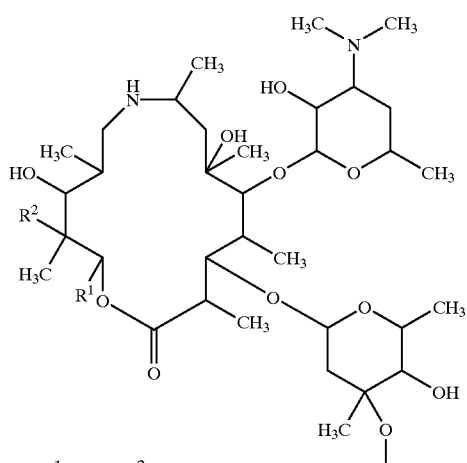

5a wherein $R^1$ and $R^2$ are as defined for the compound of formula I, with a methylating agent.

The invention also relates to the above process wherein the methylating agent is formaldehyde.

The invention also relates to a compound of the formula

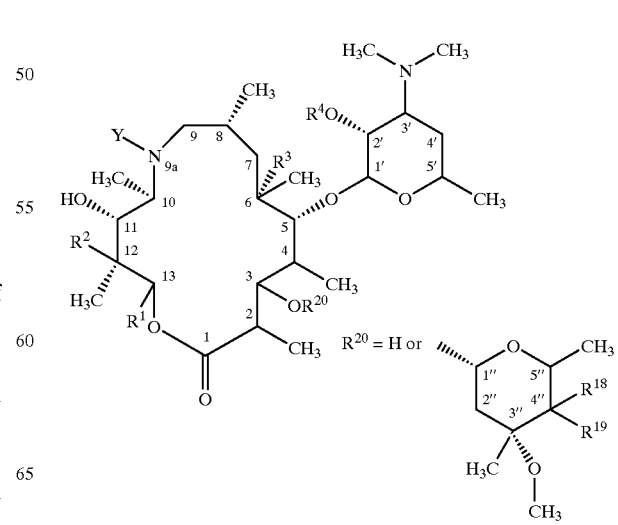

I or a pharmaceutically acceptable salt thereof, wherein:

Y is H, $C_1$–$C_{10}$ alkyl, $C_2$–$C_{10}$ alkenyl, $C_2C_{10}$ alkynyl, —$(CH_2)_mC_6$–$C_{10}$aryl, —$(CH_2)_m$(5–10 membered heteroaryl), wherein m is an integer ranging from 0 to 4, and wherein the alkyl, alkenyl, aryl, heteroaryl and alkynyl groups are optionally substituted by 1 to 3 substituents independently selected from halo, cyano, nitro, trifluoromethyl, azido, —$C(O)R^{21}$, —$OC(O)R^{21}$, —$NR^{21}C(O)R^{22}$, —$C(O)NR^{21}R^{22}$, —$NR^{21}R^{22}$, hydroxy, $C_1$–$C_6$ alkyl, $C_1$–$C_6$ alkoxy, $C_6$–$C_{10}$ aryl, and 5–10 membered heteroaryl;

$R^1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_2$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms: or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ may be with a formula (a) as shown below:

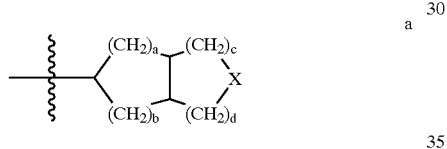

a wherein X is O, S or —$CH_2$—, a, b, c, and d are each independently an integer ranging from 0 to 2 and a+b+c+d≦5;

or $R^1$ is $CH_2R^{24}$, wherein $R^{24}$ is H, $C_1$–$C_8$alkyl, $C_2$–$C_8$alkenyl, $C_2$–$C_8$alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms: or a $C_3$–$C_8$cycloalkyl or $C_5$–$C_8$cycloalkenyl either or which may be optionally substituted by methyl or one or more $C_1$–$C_4$alkyl groups or halo atoms; or a 3 to 6 membered oxygen or sulphur containing heterocyclic ring which may be saturated or fully or partially unsaturated and which may optionally be substituted by one or more $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one or more $C_1C_4$alkyl groups or halo atoms;

$R^2$ is H or OH;

$R^3$ is H, OH, or $OCH_3$;

$R^4$ is H, —$C(O)R^9$, —$C(O)OR^9$, —$C(O)NR^9R^{10}$ or a hydroxy protecting group;

$R^5$ is —$SR^8$, —$(CH_2)_nC(O)R^8$ wherein n is 0 or 1, $C_1$–$C_{10}$ alkyl, $C_2$–$C_{10}$ alkenyl, $C_2$–$C_{10}$ alkynyl, —$(CH_2)_m$($C_8$–$C_{10}$ aryl), or —$(CH_2)_m$(5–10 membered heteroaryl), wherein m is an integer ranging from 0 to 4, and wherein the foregoing $R^5$ groups are optionally substituted by 1 to 3 $R^{16}$ groups;

each $R^6$ and $R^7$ is independently H, hydroxy, $C_1$–$C_6$ alkoxy, $C_1$–$C_6$ alkyl, $C_2$–$C_6$ alkenyl, $C_2$–$C_6$ alkynyl, —$(CH_2)_m$($C_6$–$C_{10}$ aryl), or —$(CH_2)_m$(5–10 membered heteroaryl), wherein m is an integer ranging from 0 to 4;

each $R^8$ is independently H, $C_1$–$C_{10}$ alkyl, $C_2$–$C_{10}$ alkenyl, $C_2C_{-10}$ alkynyl, —$(CH_2)_qCR^{11}R^{13}(CH_2)_rNR^{13}R^{14}$ wherein q and r are each independently an integer ranging from 0 to 3 except q and r are not both 0, —$(CH_2)_m$($C_8$–$C_{10}$ aryl), or —$(CH_2)_m$(5–10 membered heteroaryl), wherein m is an integer ranging from 0 to 4, and wherein the foregoing $R^8$ groups, except H, are optionally substituted by 1 to 3 $R^{16}$ groups;

or where $R^8$ is as —$CH_2NR^8R^{15}$, $R^{15}$ and $R^8$ may be taken together to form a 4–10 membered monocyclic or polycyclic saturated ring or a 5–10 membered heteroaryl ring, wherein said saturated and heteroaryl rings optionally include 1 or 2 heteroatoms selected from O, S and —$N(R^8)$—, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{16}$ groups;

each $R^9$ and $R^{10}$ is independently H or $C_1$–$C_6$ alkyl;

each $R^{11}$, $R^{12}$, $R^{13}$ and $R^{14}$ is independently selected from H, $C_1$–$C_{10}$ alkyl —$(CH_2)_m$($C_6$–$C_{10}$ aryl), and —$(CH_2)_m$ (5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —$(CH_2)_p$— wherein p is an integer ranging from 0 to 3 such that a 4–7 membered saturated ring is formed that optionally includes 1 or 2 carbon-carbon double or triple bonds, or $R^{13}$ and $R^{14}$ are taken together to form a 4–10 membered monocyclic or polycyclic saturated ring or a 5–10 membered heteroaryl ring, wherein said saturated and heteroaryl rings optionally Include 1 or 2 heteroatoms selected from O, S and —$N(R^8)$—, In addition to the nitrogen to which $R^{13}$ and $R^{14}$ are attached, said saturated ring optionally includes 1 or 2 carbon-carbon double or triple bonds, and said saturated and heteroaryl rings are optionally substituted by 1 to 3 $R^{16}$ groups;

$R^{15}$ is H, $C_1$–$C_{10}$ alkyl, $C_2$–$C_{10}$ alkenyl, or $C_2$–$C_{10}$ alkynyl, wherein the foregoing $R^{15}$ groups are optionally substituted by 1 to 3 substituents independently selected from halo and —$OR^9$;

each $R^{16}$ is independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)NR^6R^7$, hydroxy, $C_1$–$C_6$ alkyl, $C_{1-C_6}$ alkoxy, —$(CH_2)_m$ ($C_6$–$C_{10}$ aryl), and —$(CH_2)_m$(5–10 membered heteroaryl), wherein m is an integer ranging from 0 to 4, and wherein said aryl and heteroaryl subsituents are optionally substituted by 1 or 2 substituents independently selected from halo, cyano, nitro, trifluoromethyl, azido —$C(O)R^{17}$, —$C(O)OR^{17}$, —$OC(O)OR^{17}$, —$NR^6C(O)R^7$, —$C(O)NR^6R^7$, —$NR^6R^7$, hydroxy, $C_1$–$C_6$ alkyl, and $C_1$–$C_6$ alkoxy;

each $R^{17}$ is independently selected from H, $C_1$–$C_{10}$ alkyl, $C_2$–$C_{10}$ alkenyl, $C_2$–$C_{10}$ alkynyl, —$(CH_2)_m$($C_6$–$C_{10}$ aryl), and —(CH$_2$)$_m$(5–10 membered heteroaryl), wherein m is an integer ranging from 0 to 4, provided that R$^6$ is not H where R$^{19}$ is —CH$_2$S(O)$_n$R$^8$;

R$^{18}$ is OH;

R$^{19}$ is C$_1$–C$_{10}$ alkyl, C$_2$–C$_{10}$ alkenyl, C$_2$–C$_{10}$ alkynyl, cyano, —CH$_2$S(O)$_n$R$^8$ wherein n is an integer ranging from 0 to 2, —CH$_2$OR$^8$, —CH$_2$N(OR$^8$)R$^8$, —CH$_2$NR$^8$R$^{15}$, —(CH$_2$)$_m$(C$_5$–C$_{10}$ aryl), or —(CH$_2$)$_m$(5–10 membered heteroaryl), wherein m is an integer ranging from 0 to 4, and wherein the foregoing R$^{19}$ groups are optionally substituted by 1 to 3 R$^{16}$ groups;

or R$^{18}$ and R$^{19}$ are taken together to form an oxazolyl ring as shown below

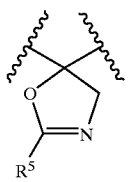

and;

each R$^{21}$ and R$^{22}$ is independently H, hydroxy, C$_1$–C$_6$ alkoxy, C$_1$–C$_6$ alkyl, C$_2$–C$_6$ alkenyl, (CH$_2$)$_m$(C$_6$–C$_{10}$) aryl, (CH$_2$)$_m$(5–10 membered heteroaryl), wherein m is an integer ranging from 0 to 4, or C$_2$–C$_{10}$ alkylyl.

The term "treatment", as used herein, unless otherwise indicated, includes the treatment or prevention of a bacterial infection or protozoa infection as provided in the method of the present invention.

As used herein, unless otherwise indicated, the term "bacterial infection(s)" or "protozoa infections; includes bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or Peptostreptococcus spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neserria gonorrheae;* toxin diseases related to infection by *S. aureus* (food poisoning and Toxic shock syndrome), or Groups A, S. and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated Mycobacterium avium complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp. odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory disease related to infection by *P. haem., P. multocida, Mycoplasma bovis,* or Bordetella spp.; cow enteric disease related to infection by *E. coli* or protozoa (i.e., coccidia, cryptosporidia, etc.), dairy cow mastitis related to infection by Staph. aureus, Strep. uberis, Strep. agalactiae, Step. dysgalactiae, Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to Infection by *Fusobacterium necrophorum* or *Bacteroides nodosus;* cow pink-eye related to infection by *Moraxella bovis,* cow premature abortion related to infection by protozoa (i.e. neosporium); urinary tract infection in dogs and cats related to infection by *E. coli;* skin and soft tissue infections in dogs and cats related to infection by Staph. epidermidis, Staph. intermedius, coagulase neg. Staph. or *P. multocida;* and dental or mouth infections in dogs and oats related to infection by Alcaligenes spp., Bacteroides spp., Clostridium spp., Enterobacter spp., Eubacterium, Peptostreptococcus, Porphfyromonas, or Prevotella. Other bacterial infections and protozoa infections and disorders related to such infections that may be treated or prevented in accord with the method of the present invention are referred to in J. P. Sanford at al., "The Sanford Guide To Antimicrobial Therapy." 26th Edition, (Antimicrobial Therapy, Inc., 1996).

The present invention also relates to a method of preparing the above compounds of formulas I, II, 8, or 9. The compounds used in the preparation of the compounds of formulas I, II, 8, and 9 can prepared using the methods described in International Application No. PCT/GB97/01810 filed Jul. 4, 1997 (Peter Francis Leadlay, James Staunton, Jesus Cortes and Michael Stephen Pacey), and International Application No. PCT/GB97/01819 filed Jul. 4, 1997 (Peter Francis Leadlay, James Staunton, and Jesus Cortes), both of which are is incorporated herein by reference in their entirety.

The present invention also relates to the compounds of formulas 2, 2a, 3, 3a, and 4 to 23 which, are useful in the preparation of the above compounds of formulas I, II, 8 and 9 and pharmaceutically acceptable salts thereof.

The term "hydroxy protecting group", as used herein, unless otherwise indicated, includes acetyl, benzyloxycarbonyl, and various hydroxy protecting groups familiar to those skilled in the art include the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo.

The term "alkyl", as used herein, unless otherwise indicated, includes saturated monovalent hydrocarbon radicals having straight, cyclic or branched moieties, or mixtures thereof. It is to be understood that where cyclic moieties are intended, at least three carbons in said alkyl must be present. Such cyclic moieties include cyclopropyl, cyclobutyl and cyclopentyl.

The term "alkoxy", as used herein. unless otherwise indicated, includes —O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "5–10 membered heteroaryl", as used herein, unless otherwise indicated, includes aromatic heterocyclic groups containing one or more heteroatoms each selected from O, S and N, wherein each heterocyclic group has from 5 to 10 atoms in its ring system, Examples of suitable 5–10 membered heteroaryl groups include pyridinyl, imidazolyl, pyrimidinyl, pyrazolyl, (1,2,3,)- and (1,2,4)-triazolyl, pyrazinyl, tetrazolyl, furyl, thienyl, isoxazolyl, oxazolyl, pyrrolyl and thiazolyl.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride, hydrobromide, hydrolodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of be compounds of the present invention.

Certain compounds of the present invention may have asymmetric centers and therefore exist in different enantiomeric and diastereomeric forms. This invention relates to the use of all optical isomers and stereoisomers of the compounds of the present invention, and mixtures thereof, and to all pharmaceutical compositions and method; of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of of the present invention may be prepared according to Schemes 1–4 below and the description that follows. In the following Schemes, unless otherwise indicated, substituents $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and Y are as defined above.

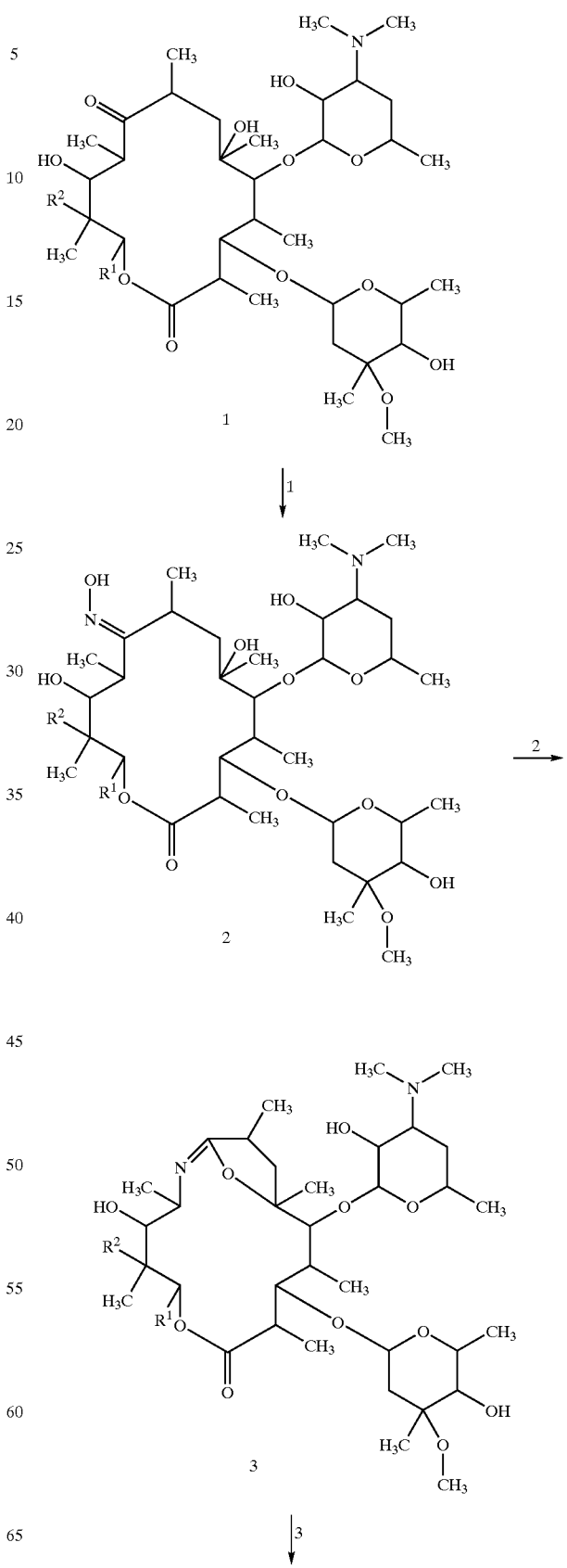

Scheme 1

-continued
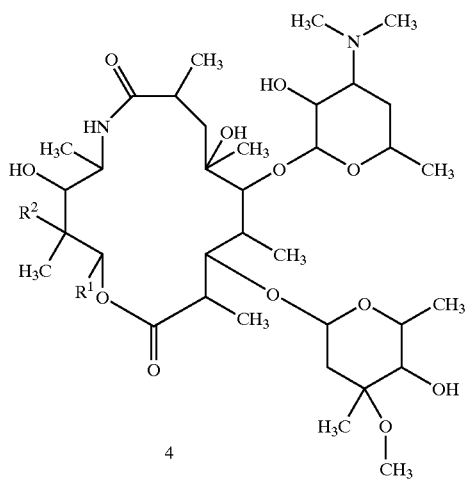
4
+
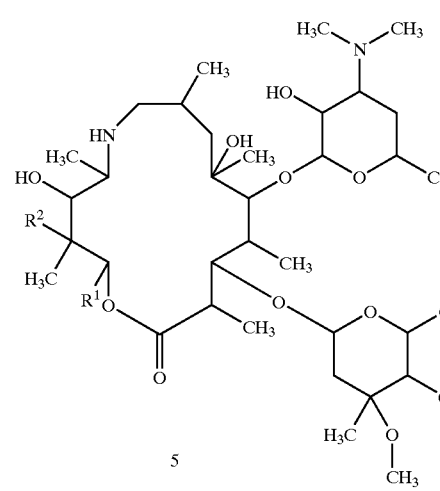
5
↓ 4
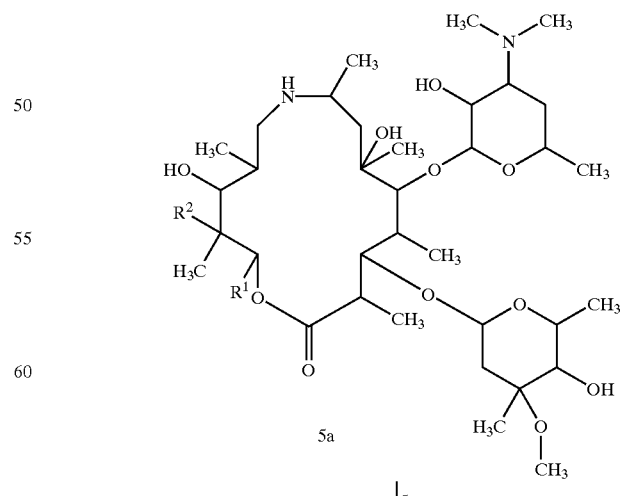
6
Scheme 2
1 →(1)→ 2
↓ 2a
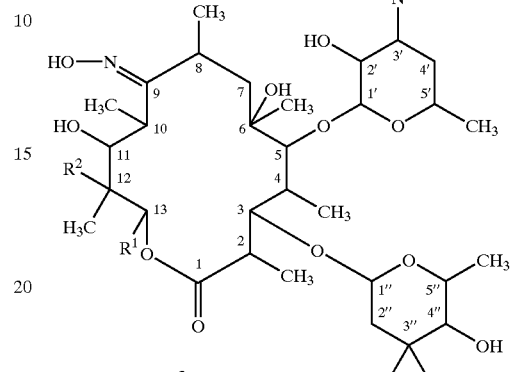
2a
↓ 3a
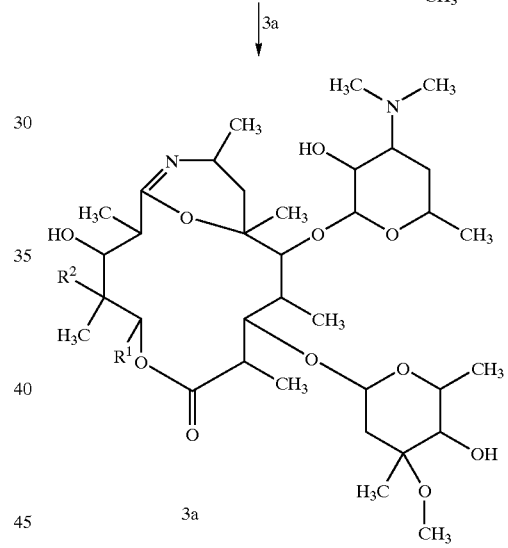
3a
→(4a)→
5a
↓ 5a -continued
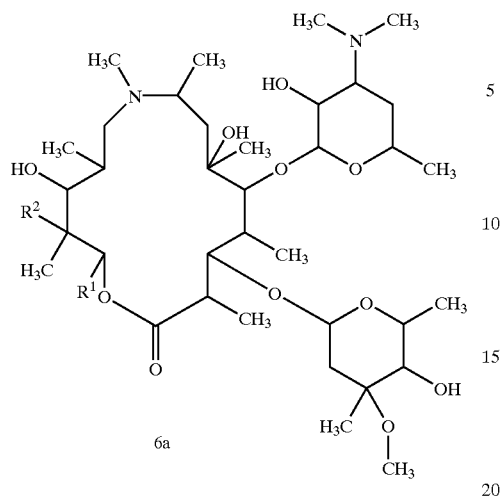
6a
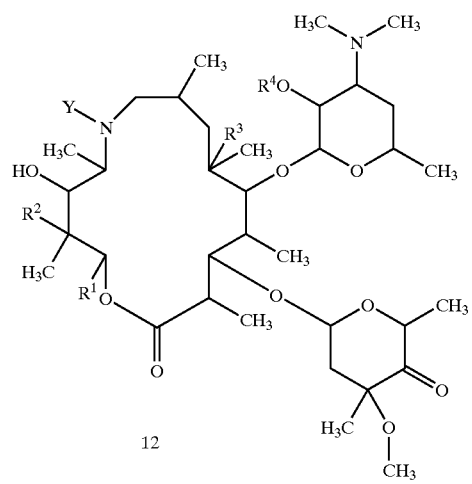
12
Scheme 3A
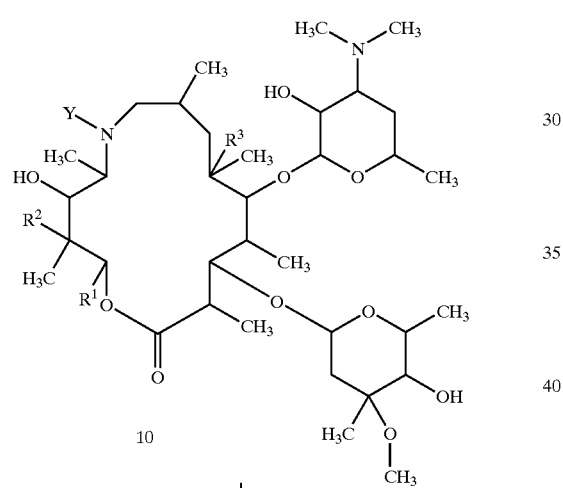
10
↓ 1
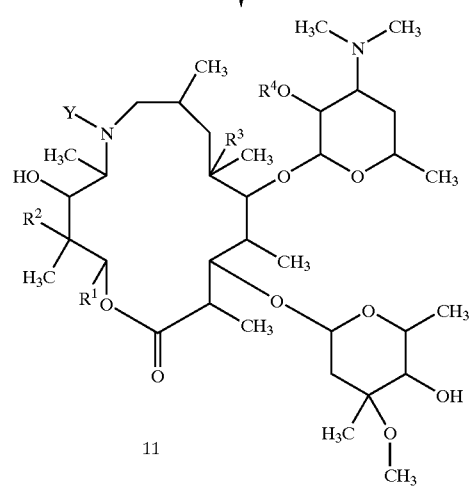
11
↓ 2
Scheme 3B
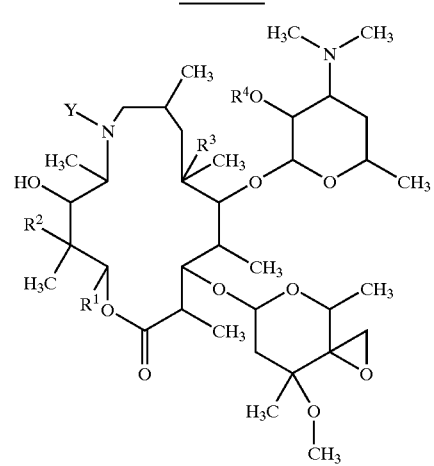
13
↓ 1
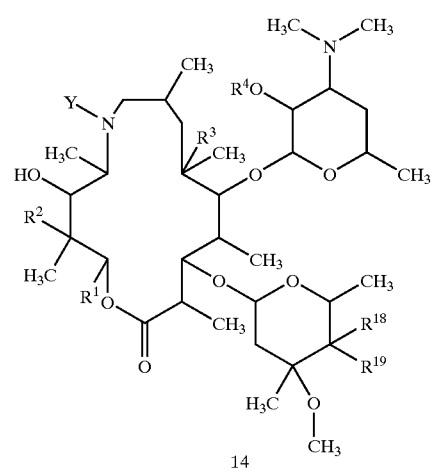
14

Scheme 4
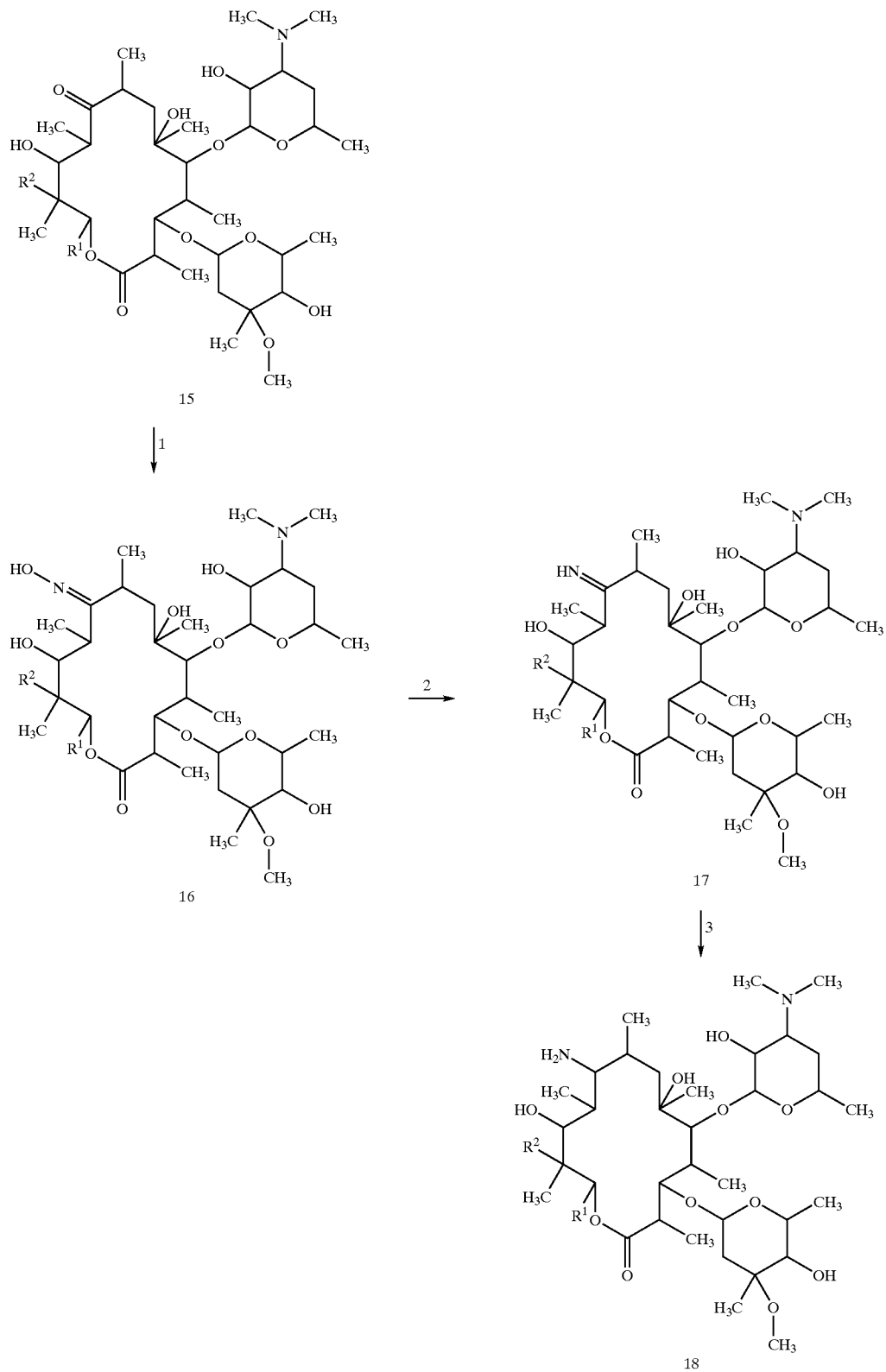

The compounds of the present invention are readily prepared. The compounds used in the preparation of the compounds of formulas I, II, 8, and 9 can prepared using the methods described in International Application No. PCT/GB97/01810 filed Jul. 4, 1997 (Peter Francis Leadlay, James Staunton, Jesus Cortes and Michael Stephen Pacey), and International Application No. PCT/GB97/01819 filed Jul. 4, 1997 (Peter Francis Leadlay, James Staunton, and Jesus Cortes), both of which are is Incorporated herein by reference in their entirety.

The novel polyketides and methods and means for preparing them, and specifically the novel macrolides that are useful in the preparation of the compounds of the present invention are prepared by fermenting suitable organisms in the presence of $R_1CO_2H$, where $R^1$ is as defined in claim 1 or claim 2. A preferred organism is *Saccharopolyspora erythraea* preferably containing an integrated plasmid capable of directing synthesis of desired compounds. In producing such novel polyketides, polyketide biosynthetic genes or portions of them, which may be derived from different polyketide biosynthetic gene clusters are manipulated to allow the production of novel erythromycins, Polyketides are a large and structurally diverse class of natural products that includes many compounds possessing antibiotic or other pharmacological properties, such as erythromycin, tetracyclines, rapamycin, avermectin, polyether ionophores, and FK506. In particular, polyketides are abundantly produced by Streptomyces and related actinomycete bacteria. They are synthesised by the repeated stepwise condensation of acylthioesters in a manner analogous to that of fatty acid biosynthesis. The greater structural diversity found among natural polyketides arises from the selection of (usually) acetate or propionate as "starter" or "extender" units; and from the differing degree of processing of the β-keto group observed after each condensation. Examples of processing steps include reduction to β-hydroxyacyl-, reduction followed by dehydration to 2-enoyl-, and complete reduction to the saturated acylthioester. The stereochemical outcome of these processing steps is also specified for each cycle of chain extension. The biosynthesis of polyketides is initiated by a group of chain-forming enzymes known as polyketide synthases. Two classes of polyketide synthase (PKS) have been described in actinomycetes. However, the novel polyketides and processes which are used in preparing the compounds of the present invention are synthesised by Type I PKS's, represented by the PKS's for the macrolides erythromycin, avermectin and rapamycin, and consist of a different set or "module" of enzymes for each cycle of polyketide chain extension (Cortes, J. et al. Nature (1990) 348:176–176; Donadio, S. et al. Science (1991) 252:675–679; MacNeil, D. J. et al. Gene (1992), 115:119–125, Schwecke, T. et al. Proc. Natl. Acad, Sci. USA (1995) 92:7839–7843). Note: The term "natural module" as used herein refers to the set of contiguous domains, from a β-ketoacylsynthase ("KS") gene to the next acyl carrier protein ("ACP") gene, which accomplishes one cycle of polyketide chain extension. The term "combinatorial module" is used to refer to any group of contiguous domains (and domain parts), extending from a first point in a first natural module, to a second equivalent point in a second natural module. The first and second points will generally be in core domains which are present in all modules, i.e., both at equivalent points of respective KS, AT (acyl transferase), ACP domains, or in linker regions between domains.

The organisation of the erythromycin producing PKS, (also known as β-deoxyerythronolide B synthase, DEBS) genes contains three open reading frames encode the DEBS polypeptides. The genes are organised in six repeated units designated modules. The first open reading frame encodes the first multi-enzyme or cassette (DEBS1) which consists of three modules: the loading module (ery-load) and two extension modules (modules 1 and 2). The loading module comprises an acyl transferase and an acyl carrier protein. This may be contrasted with FIG. 1 of WO93/13663 (referred to below). This shows ORF1 to consist of only two modules, the first of which is in fact both the loading module and the first extension module.

In-frame deletion of the DNA encoding part of the ketoreductase domain of module 5 in DEBS has been shown to lead to the formation of erythromycin analogues 5,6-dideoxy-3-mycarosyl-5-oxoerythronolide B, 5,6-dideoxy-5oxoerythronolide B and 5,6-dideoxy6,6epoxy-5-oxoerythronolide B (Donadio, S. et al. Science, (1991) 252:675–679). Likewise, alteration of active site residues in the enoylreductase domain of module 4 in DEBS, by genetic engineering of the corresponding PKS-encoding DNA and its introduction into *Saccharopolyspora erythraea,* led to the production of 6,7-anhydroerythromycin C (Donadio S. et al. Proc. Natl. Acad. Sci. USA (1993) 90:7119–7123).

International Patent Application number WO 93/13663, which is incorporated herein by reference In Its entirety, describes additional types of genetic manipulation of the DEBS genes that are capable of producing altered polyketides. However, many such attempts are reported to have been unproductive (Hutchinson C. R. and Fujii, I. Annu. Rev. Microbiol. (1995) 49:201–238, at p.231). The complete DNA sequence of the genes from *Streptomyces hygroscopicus* that encode the modular Type 1 PKS governing the biosynthesis of the macrocyclic immunosuppressant polyketide rapamycin has been disclosed (Schwecke, T. et al. (1995) Proc. Natl. Acad. Sci. USA 92:7839–7843). The DNA sequence is deposited in the EMBL/Genbank Database under the accession number X86780.

The complex polyketides produced by modular Type I PKS's are particularly valuable, in that they include compounds with known utility as anthelminthics, insecticides, immunosuppressants, antifungal, and/or antibacterial agents. Because of their structural complexity, such novel polyketides are not readily obtainable by total chemical synthesis, or by chemical modifications of known polyketides. As described in International Application PCT/GB97/01810, the Type I PKS gene assembly encodes a loading module which is followed by extension modules. It is particularly useful to provide a hybrid PKS gene assembly in which the loading module is heterologous to the extension modules and is such as to lead to a polyketide having an altered starter unit. As noted in in International Application PCT/GB97/01810, this is a concept quite unknown to the prior art since this does not recognise the existence of loading modules. WO93/13653 refers to altering PKS genes by inactivating a single function (i.e. a single enzyme) or affecting "an entire module" by deletion, insertion, or replacement thereof. The loading assembly, in their terms, is not a module.

If the loading module is one which accepts many different carboxylic acid units, then the hybrid gene assembly can be used to produce many different polyketides. For example, a hybrid gene assembly may employ nucleic acid encoding an avr loading module with ery extender modules. A loading module may accept unnatural acid units and derivatives thereof, the avr loading module is particularly useful in this regard (Dutton et al., (1991) J. Antibiot., 44:357–365). In addition, it is possible to determine the specificity of the natural loading module for unnatural starter units and to take advantage of the relaxed specificity of the loading module to generate novel polyketides. Thus, International Application PCT/GB97/01810 describes the unexpected ability of the ery loading module to incorporate unnatural carboxylic acids and derivatives thereof to produce novel erythromycins in erythromycin-producing strains containing only DEBS genes. Of source one may also make alterations within a product polyketide particularly by replacing an extension module by one that gives a ketide unit at a different oxidation state and/or with a different stereochemistry. It has generally been assumed that the stereochemistry of the methyl groups in the polyketide chain is determined by the acyltransferase, but it is, in fact, a feature of other domains of the PKS and thus open to variation only by replacement of those domains, individually or by module replacement. Methyl and other substituents can be added or removed by acyltransferase domain replacement or total module replacement Consequently, it also becomes apparent to those skilled in the art that it is possible to combine be use of the relaxed substrate specificity of the erythromycin loading module with extension module replacement and hybrid loading module substitution with extension module replacement as a mechanism to produce a wide range of novel erythromycins. Thus, International Application PCT/GB97/01810 describes the production of novel erythromycins by non-transformed organisms and also such gene assemblies, vectors containing such gene assemblies, and transformant organisms that can express them to produce novel erythromycins in transformed organisms. Transformant organisms may harbour recombinant plasmids, or the plasmids may integrate. A plasmid with an int sequence will integrate into a specific attachment site (att) of a host's chromosome. Transformant organisms may be capable of modifying the initial products, e.g., by carrying out all or some of the biosynthetic modifications normal in the production of erythromycins. However, use may be made of mutant organisms such that some of the normal pathways are blocked. e.g., to produce products without one or more "natural" hydroxy-groups or sugar groups, for instance as described in WO 91/16334 or in Weber et al. (1985) J. Bacteriol. 164:425–433 which are incorporated herein by reference in their entirety. Alternatively, use may be made of organisms in which some of the normal pathways are overexpressed to overcome potential rate-limiting steps in the production of the desired product, for instance as described in WO 97/06266 which is incorporated herein by reference in its entirely.

This aspect of the method is largely concerned with treating PKS gene modules as building blocks that can be used to construct enzyme systems, and thus novel erythromycin products, of desired types. This generally involves the cutting out and the assembly of modules and multi-module groupings. Logical places for making and breaking intermodular connections are be In the linking regions between modules. However, it may be preferable to make cuts and joins actually within domains (i.e., the enzyme-coding portions). close to the edges thereof. The DNA is highly conserved here between all modular PKS's, and this may aid in the construction of hybrids that can be transcribed. It may also assist in maintaining the spacing of the active sites of the encoded enzymes, which may be important For example, in producing a hybrid gene by replacing the ery a loading module by an avr loading module, the ery module together with a small amount of the following ketosynthase (KS) domain was removed. The start of the KS domain (well spaced from the active site) is highly conserved and therefore provides a suitable splicing site as an alternative to the linker region between the loading domain and the start of the KS domain. The excised ery module was then replaced by an avr loading module.

In fact, when substituting a loading module, it may be desirable to replace not just the loading module domains (generally acyl transferase (AT) and acyl carrier protein (ACP)), but also the KS at the start of the following extension module. Typically, the excised loading module would have provided a propionate starter, and the replacement is intended to provide one or more different starters. Propionate, however, may feed into the KS of the extension module from a propionate pool in the host cell, leading to dilution of the desired products. This can be largely prevented by substituting an extended loading module including all or most of the KS domain. (The splice site may be in the end region of the KS gene, or early in the following AT gene, or the linker region between them.)

When replacing "modules", one is not restricted to "natural" modules. For example, a "combinatorial module" to be excised and/or replaced and/or inserted may extend from the corresponding domain of two natural-type modules, e.g., from the AT of one module to the AT of the next, or from KS to KS. The splice sites will be in corresponding conserved marginal regions or in linker regions. A combinatorial module can also be a 'double' or larger multiple, for adding 2 or more modules at a time.

International Application PCT/GB97/01810 describes novel erythromycins obtainable by means of the previous aspects. These include the following:

(i) An erythromycin analogue (being a macrolide compound with a 14-membered ring) in which a substituent R, on the C-13 position, bears a side-chain other than ethyl, generally a straight chain C3–C6 alkyl group, a branched $C_3$–$C_8$ alkyl group, a $C_3$–$C_8$ cycloalkyl or cyloalkenyl group (optionally substituted, e.g., with one or more hydroxy, $C_{1-4}$ alkyl or alkoxy groups or halogen atoms), or a 3–6 membered heterocycle containing O or S, saturated or fully or partially unsaturated, optionally substituted (as for cycloalkyl), or R is phenyl which may be optionally substituted with at least one substituent selected from $C_1$–$C_4$ alkyl, $C_1$–$C_4$ alkoxy and $C_1$–$C_4$ alkylthio groups, halogen atoms, trifluoromethyl, and cyano, or R may be a group with a formula (a) as shown below:

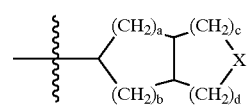

a wherein X is O, S or —$CH_2$—, a, b, c, and d are each Independently 0–2 and a+b+c+d$\leq$5. Preferred candidates for the C-13 substituent R are the groups of carboxylate units RCOOR', usable as substrates by an avr starter module, or rapamycin starter variants. Preferred substrates are the carboxylic acids RCOOH. Alternative substrates that can be effectively used are carboxylic acid salts, carboxylic acid esters, or amides. Preferred esters are N-acetyl-cysteamine thioesters which can readily be utilized as substrates by the avr starter module as illustrated by Dutton at al. in EP 0350187 which is incorporated herein by reference in its entirety. Preferred amides are N-acyl imidazoles. Other alternative substrates that may be used are derivatives which are oxidative precursors for the carboxylic acids; thus, for example suitable substrates would be amino acids of the formula $RCH(NH_2)COOH$, glyoxylic acids of the formula RCOCOOH, methylamine derivatives of the formula $RCH_2NH_2$, methanol derivatives of the formula $RCH_2OH$, aldehydes of the formula RCHO or substituted alkanoic acids of the formula $R(CH_2)_nCOOH$ wherein n is 2, 4, or 6. Thus examples of preferred substrates include isobutyrate (Risi-Pr) and 2-methylbutyrate (Ris1-methylpropyl). Other possibilities include n-butyrate, cyclopropyl carboxylate, cyclobutyl carboxylate, cyclopentyl carboxylate cyclohexyl carboxylate, cycloheptanyl carboxylate, cyclohexenyl carboxylates, cycloheptenyl carboxylates, and ring-methylated variants of the cyclic carboxylates and the aforementioned derivatives thereof.

The erythromycin analogue may correspond to the initial product of a PKS (6-deoxyerythronolide) or the product after one or more of the normal biosynthetic steps. These comprise: 6-hydroxylation; 3-0-glycosylation: 5-0-glycosylation; 12-hydroxylation: and specific sugar methylation.

Thus, the analogues may include those corresponding to 6-deoxyerythronolide B, erythromycin A, and various intermediates and alternatives thereof.

(ii) Erythromycin analogues differing from the corresponding 'natural' in the oxidation state of one or more of the ketide units (i.e. selection of alternatives from the group: —CO—, —CH(OH)—, is CH—, and $CH_2$—)

The stereochemistry of any —CH(OH)— is also independently selectable.

(iii) Erythromycin analogues differing from the corresponding 'natural' compound in the absence of a 'natural' methyl side-chain. (This is achievable by use of a variant AT). Normal extension modules use either $C_2$ or $C_3$ units to provide unmethylated and methylated ketide units. One may provide unmethylated units where methylated units are natural (and vice versa, in systems where there are naturally unmethylated units) and also provide larger units, e.g., $C_4$ to provide ethyl substituents.

(iv) Erythromycin analogues differing from the corresponding 'natural' compound in the stereochemistry of 'natural' methyl; and/or ring substituents other than methyl.

(v) Erythromycin analogues having the features of two or more of sections (i) to (iv).

(vi) Derivatives of any of the above which have undergone further processing by non-PKS enzymes, e.g., one or more of hydroxylation, epoxidation, glycosylation, and methylation.

International Application PCT/GB97/01810 describes methods for the production of the novel erythromycins useful in the preparation of the compounds of the present invention. In the simplest method, unnatural starter units (preferably, but not restricted to the carboxylic acid analogues of the unnatural starter units) are introduced to untransformed organisms capable of producing erythromycins. A preferred approach involves introduction of the starter unit into fermentation broths of the erythromycin-producing organism, an approach which is more effective for transformed organisms capable of producing erythromycins, However, the starter unit analogue can also be introduced to alternative preparations of the erythromycin producing organisms, for example, fractionated or unfractionated broken-cell preparations. Again, this approach is equally effective for transformed organisms capable of producing erythromycins. In another method, one or more segments of DNA encoding individual modules or domains within a heterologous Type I PKS (the "donor" PKS) have been used to replace the DNA encoding, respectively, Individual modules or domains within the DEBS genes of an erythromycin-producing organism. Loading modules and extension modules drawn from any natural or non-natural Type I PKS, are suitable for this "donor" PKS but particularly suitable for this purpose are the components of Type I PKS's for the biosynthesis of erythromycin, rapamycin, avermectin, tetronasin, oleandomycin, monensin, amphotericin, and rifamycin, for which the gone and modular organisation is known through gone sequence analysis, at least in part. Particularly favourable examples of the loading modules of the donor PKS are those loading modules showing a relaxed specificity, for example, the loading module of the avermectin (avr)-producing PKS of Streptomyces avermitilis; or those loading modules possessing an unusual specificity, for example, the loading modules of the rapamycin-, FK506- and ascomycin-producing PKS's. all of which naturally accept a shlkimate-derived starter unit. Unexpectedly, both the untransformed and genetically engineered erythromycin-producing organisms when cultured under suitable conditions have been found to produce non-natural erythromycins, and where appropriate, the products are found to undergo the same processing as the natural erythromycin.

International Application PCT/GB97/01810 further describes a plasmid containing "donor" PKS DNA is introduced into a host cell under conditions where the plasmid becomes integrated into the DEBS genes on the chromosome of the erythromycin-producing strain by homologous recombination, to create a hybrid PKS. A preferred embodiment is when the donor PKS DNA includes a segment encoding a loading module in such a way that this loading module becomes linked to the DEBS genes on the chromosome. Such a hybrid PKS produces valuable and novel erythromycin products when cultured under suitable conditions as described herein. Specifically, when the loading module of the DEBS genes is replaced by the loading module of the avermectin-producing (avr) PKS, the novel erythromycin products contain a starter unit typical of those used by the avr PKS. Thus, when the loading module of the ery PKS is replaced by the avr loading module, *Saccharopolyspora erythraea* strains containing such hybrid PKS are found to produce 14-membered macrolides containing starter units typically used by the avr PKS.

As noted in International Application PCT/GB97/01810, it is unexpected that the 14-membered macrolide polyketides produced by such recombinant cells of *S. erythraea* are found to include derivatives of erythromycin A, showing that the several processing steps required for the transformation of the products of the hybrid PKS into novel and therapeutically valuable erythromycin A derivatives are correctly carried out. International Application PCT/GB97/01810 describes the unexpected and surprising finding that transcription of any of the hybrid erythromycin genes can be specifically increased when the hybrid genes are placed under the control of a promoter for a Type II PKS gene linked to a specific activator gene for that promoter. It is particularly remarkable that when a genetically engineered cell containing hybrid erythromycin genes under such control is cultured under conditions suitable for erythromycin production, significantly enhanced levels of the novel erythromycin are produced. Such specific increases in yield of a valuable erythromycin product are also seen for natural erythromycin PKS placed under the control of a Type II PKS promoter and activator gene. In a preferred embodiment, desired genes present on an SCP2*-derived plasmid are placed under the control of the bidirectional actI promoter derived from the actinorhodin biosynthetic gene cluster of *Streptomyces coelicolor*, and in which the vector also contains the structural gene encoding the specific activator protein Act II-orf 4. The recombinant plasmid is introduced into *Saccharopolyspora erythraea*, under conditions where either the introduced PKS genes, or PKS genes already present in the host strain, are expressed under the control of the actII promoter.

Such strains produce the desired erythromycin product and the activator gene requires only the presence of the specific promoter in order to enhance transcriptional efficiency from the promoter. This is particularly surprising in that activators of the ActII-orf4 family do not belong to a recognised class of DNA-binding proteins. Therefore it would be expected that additional proteins or other control elements would be required for activation to occur in a heterologous host not known to produce actinorhodin or a related isochromanequinone pigment. It is also surprising and useful that the recombinant strains can produce more than ten-fold erythromycin product than when the same PKS genes are under the control of the natural promoter, and the specific erythromycin product is also produced precociously in growing culture, rather than only during the transition from growth to stationary phase, Such erythromycins are useful as antibiotics and for many other purposes in human and veterinary medicine. Thus, when the genetically engineered cell is *Saccaropolyspora erythraea,* the activator and promoter are derived from the actinorhodin PKS gene cluster and the actI/actII-orf4-regulated ery PKS gene cluster is housed in the chromosome, following the site-specific integration of a low copy number plasmid vector, culturing of these cells under suitable conditions can produce more than ten-fold total 14-membered macrolide product than in a comparable strain not under such heterologous control. When in such a genetically engineered cell of *S. erythraea* the PKS genes under this heterologous control are hybrid Type I PKS genes whose construction is described herein, more than ten-fold hybrid polyketide product can be obtained compared to the same hybrid Type I PKS genes not under such control. Specifically, when the hybrid Type I PKS genes are the ery PKS genes in which the loader module is replaced by the avr loading module, a ten-fold increase is found in the total amounts of novel 14-membered macrolides produced by the genetically engineered cells when cultured under suitable conditions as described in PCT/GB97/01810.

The suitable and preferred means of growing the untransformed and genetically-engineered erythromycin-producing cells, and suitable and preferred means for the isolation, identification, and practical utility of the novel erythromycins are described more fully, in International Application PCT/GB97/01810.

Erythromycin analogus described in International Application PCT/GB97/01810 are produced by fermentation of an untransformed or transformed organism capable of producing erythromycins, including but not limited to Saccaropolyspora species, *Streptomyces griscoplanus,* Nocardia sp., Micromonospora sp, Arthobacter sp., and *Streptomyces antibioticus,* but excluding *S. coelicolor.* Particularly suitable in this regard are untransformed and transformed strains of *Saccaropolyspora erythraea,* for example NRRL 2338, 18643, 21484. Particularly preferred transformed strains are those in which the erythromycin loading module has been replaced with the loading module from the avermectin producer, *Streptomyces avermitilis,* or the rapamycin producer, *Streptomyces hygroscopicus.* The preferred method of producing compounds of the current invention is by fermentation of the appropriate organism in the presence of the appropriate carboxylic acid of the formula $R_1COOH$, wherein $R_1$ is as defined in formulae 1 or 2 of International Application PCT/GB97/01810 or is $R^1$ of the compounds of the present invention, or a salt, ester (particularly preferable being the N-acetylcysteamine thioester), or amide thereof or oxidative precursor thereof. The acid or derivative thereof is added to the fermentation either at the time of inoculation or at intervals during the fermentation. Production of the compounds of this invention may be monitored by removing samples from the fermentation, extracting with an organic solvent and following the appearance of the compounds of this invention by chromatography, for example using high pressure liquid chromatography. incubation is continued until the yield of the compound of formulae 1 or 2 has been maximised, generally for a period of 4 to 10 days. A preferred level of each addition of the carboxylic acid or derivative thereof is between 0.05 and 4.0 g/L. The best yields of the compounds from formulae 1 or 2 are generally by gradually adding the acid or derivative to the fermentation, for example by daily addition over a period of several days. The medium used for the fermentation may be a conventional complex medium containing assimilable sources of carbon, nitrogen and trace elements.

The wide range of starter units accepted by the avr loading module has been comprehensively established in previous studies (for example European Patent Applications 0 214 731, 0 350 187, 0 317 146 which are incorporated herein in their entirety). Consequently, it should be understood that the invention is not limited to the specific detail of these examples and simply serve to confirm the effectiveness of the avr loading module. Furthermore, the examples using the pIG1or pND30 construct clearly demonstrate the capability of the actI promoter and its cognate activator gene actII-orf4 to ehance the expression of the novel compounds of this invention when linked to the avr loading module. It is also apparent from the examples that untransformed strains of *Saccharopolyspora erythraea* are also readily capable of taking up exogenously-supplied substrates to generate novel erythromycin polyketides. Consequently, it is also apparent to those skilled in the art that specific novel compounds of this invention can be readily produced by selection of the appropriate erythromycin producing strain (optionally incorporating the pIG1 or pND30 plasmid into the desired strain), and supplementing the fermentation with the appropriate starter unit. Thus, 6-deoxyerythromycin and 6,12dideoxyerythromycin derivatives of the present invention can be readily produced using *Saccharopolyspora erythraea* NRRL 18643 or NRRL 21484 as indicated in U.S. Pat. No. 5,141,926 and WO 97/06268. Similarly, use of the *Saccharopolyspora erythraea* strains described by Weber et al. in J. Bacteriol., 164:425–433, 1991 can also be employed to obtain the desired novel analogues of the present invention. For example, stain UW24 can be used (optionally transformed by pIG1 or pND30) to obtain novel analogues of erythronolide B.

In step 1 of Scheme 1, the C-9 carbonyl, of formula 1, is converted to the corresponding oxime at the C-9 position by reacting the macrolide with hydroxylamine or preferably a hydroxylamine salt such as a hydrochloride. Under presently preferred conditions, at least one molar equivalent, usually an excess, 5–10 equivalents, is usually employed in a weakly basic, tertiary amine (preferably pyridine) as a solvent; at a temperature range 20–80° C. A protic solvent, such as methanol, can also be used in conjunction with a base such as barium carbonate, to provide a weakly basic solvent.

In step 2 of Scheme 1, oxime, of formula 2, is rearranged to the corresponding imino ether via a Beckman rearrangement as outlined in J. Chem, Soc. Perkin Trans. I, 1986, 1181. The preferred conditions employ an excess, (2–4 molar equivalents) of an orgnic sulfonyl chloride, preferably p-toluene-sulfonyl chloride, which is reacted with the oxime, as free base or acid salt) in a mixture of a lower ketone, such as methyl ethyl ketone or acetone, and water containing a large molar excess of sodium bicarbonate, at a temperature of 0–50° C., preferably at 0–30° C.

In step 3 of Scheme 1, Imino ether, of formula 3,is reduced to a mixture of the lactam, of formula 4, and the azalide, of formula 5. This can be accomplished in various methods familiar to those skilled in the art. One such method is catalytic hydrogenation employing a reducing agent such as an organo-metallic catalyst such as platinum oxide in an acid solvent such as glacial acetic acid under a minimum of 50 psi hydrogen pressure. A preferred method for the production of 6 incorporates the use of boron reducing reagents such as sodium borohydride, generally used in excess, 2–10 equivalents, in protic solvents such as methanol or ethylene glycol, at a temperature range of −5–40° C., preferably 0–20° C.

In step 4 of Scheme 1, azalide, of formula 5, is converted to formula 6 via reductive methylation, using a methylating agent such as formaldehyde in the presence of a reducing agent preferably formic acid. The preferred method requires at least one molar equivalent each of formaldehyde and formic acid in an inert solvent such as chloroform at 20–100° C., preferably at 30–60° C.

In step 1 of Scheme 2, the C-9 carbonyl, of formula 1, is converted to the corresponding oxime at the C-9 position by reacting the macrolide with hydroxylamine or preferably, a hydroxylamine salt such as a hydrochloride. Under presently preferred conditions, at least one molar equivalent, usually an excess, 5–10 equivalents, is usually employed in a weakly basic, tertiary amine (preferably pyridine) as a solvent, at a temperature range 20–80° C. A protic solvent, such as methanol, can also be used in conjunction with a base, such as barium carbonate, to provide a weakly basic solvent.

In step 2a of Scheme 2, oxime, of formula 2, where the olefin geometry is preferentially the "E" isomer is converted to the "Z" isomer in protic solvents such as ethanol using bases of sufficient strength to substantially deprotonate the 9E oxime with small counter ions, such as Li$^+$ or Na$^+$, such as lithium hydroxide.

In step 3a of Scheme 2, oxime, of formula 2a, is rearranged to the corresponding imino ether via a Beckman rearrangement as outlined In J. Chem. Soc. Perkin Trans. I, 1986, 1181, The preferred conditions employ an excess, 2–4 molar equivalents) of an orgnic sulfonyl chloride, preferably p-toluene-sulfonyl chloride, which is reacted with the oxime, as free base or acid salt) in a mixture of a lower ketone, such as methyl ethyl ketone or acetone, and water containing a large molar excess if sodium bicarbonate, at a temperature of 0–50° C., preferably at 0–30° C.

In step 4a of Scheme 2, imino ether, of formula 3a, is reduced to the azalide, of formula 5a. This can be accomplished in various methods familiar to those skilled in the art. One such method is catalytic hydrogenation employing a reducing agent such as an organo-metallic catalyst such as for example, platinum oxide, in an acid solvent such as glacial acetic acid under a minimum of 50 psi hydrogen pressure. A preferred method for the production of incorporates the use of boron reducing reagents such as sodium borohydride, generally used in excess, 2–10 equivalents, in protic solvents such as methanol or ethylene glycol, at a temperature range of $-5$–40° C., preferably 0–20° C.

In stop 5a of Scheme 2, azalide, of formula 5a, is converted to formula 6a via reductive methylation, using a methylating agent such as formaldehyde, in the presence of a reducing agent, preferably formic acid. The preferred method requires at least one molar equivalent each of formaldehyde and formic acid in an inert solvent such as chloroform at 20–100° C., preferably at 30–60° C.

In step 1 of Scheme 3A, the C-2' hydroxy group may be selectively protected by treating the compound of formula 10 with one equivalent of acetic anhydride in dichloromethane in the absence of external base to provide the compound of formula 11 wherein $R_4$ is acetyl. The acetyl protecting group may be removed by treating the compound of formula 11 with methanol at 23–65° C. for about 10 to about 48 hours. The C-2' hydroxy may also be protected with other protecting groups such as the benzyloxycarbonyl (Cbz) group using methods familiar to those skilled in the art The C-9a amino group may also require protection when Y is H before further synthetic modifications are performed. Suitable protecting groups for the amino moiety are Cbz and t-butyloxycarbonyl (Boc) groups. To protect the C9a amino group, the macrolide may be treated with t-butyl dicarbonate in anhydrous tetrahydrofuran (THF) or benzyloxycarbonyl N-hydroxysuccinimide ester or benzylchloroformate to protect the amino group as its t-butyl or benzyl carbamate. Both the C-9a and the C-2' bydroxy may be selectively protected with the Cbz group in one step by treating the compound of formula 10, where Y is a hydrogen, with benzylchloroformate in THF and water. The Boc group may be removed by acid treatment and the Cbz group may be removed by conventional catalytic hydrogenation. In the following description, it is assumed that the C-9a amino moiety and the C-2' hydroxy group are protected and deprotected as would be deemed appropriate by one skilled in the art.

In step 2 of Scheme 3A, the C4" hydroxy group of the compound of formula 11 is oxidized to the corresponding ketone, formula 12, by methods familiar to those skilled in the art Compounds of formula 14 can be generated by treating compounds of formula 12 with $R_{19}MgX_1$ or $R_{19}$-Li and $Mg(X_1)_2$, wherein $X_1$ is a halide such as chloro or bromo, in a solvent such as THF, ethylene glycol, dimethyl ether (DME), diisopropyl ether, toluene, diethyl ether, or tetramethylethylenediamine (TMEDA), or a mixture of the foregoing solvents, preferably an ether solvent, at a temperature ranging from about $-78°$ C. to about room temperature (20–25° C.).

Scheme 3B illustrates the preparation of compounds of formula 14 using an epoxide intermediate. In Scheme 3B, the compound of formula 13 may be generated by two methods. By treating the compound of formula 12 with $(CH_3)_3S(O)X^2$, wherein X is halo, $-BF_4$, or $PF_6$, preferably iodo, in the presence of a base such as potassium tert-butoxide, sodium ethoxide, sodium hydride, 1,1,3, 3tetramethylguanidine, 1,8-diazabicyclo[5.4.0]undec-7-ene, 1,5-diazabicylo[4.3.0]non-5-ene, potassium ethoxide, or sodium methoxide, preferably a sodium-containing base such as sodium hydride, in a solvent such as THF, an ether solvent, dimethylformamide (DMF), or methyl solfoxide (DMSO), or a mixture of the foregoing solvents, at a temperature range of about 0° C. to about 60° C., the compound of formula 13 is generated In which the following configuration of the epoxide moiety may predominate:

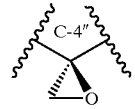

By treating the compound of formula 12 with $(CH_3)_3SX^3$, wherein $X^3$ is halo, $-BF_4$, $-PF_6$, preferably $-BF_4$, in the presence of a base such as potassium tert-butoxide, sodium ethoxide, sodium hydride, 1,1,3,3-tetramethylguanidine, 1,8diazabicylco[5.4.0]undec7-ene, 1,5-diazabicylo[4.3.0] non-5-ene, potassium ethoxide, potassium t-butoxide, KHMDS or sodium methoxide, preferably KHMDS. In a solvent such as THF, an ether solvent, dimethylformamide (DMF), or methyl sulfoxide (DMSO), or a mixture of the foregoing solvents, at a temperature range of about 0° C. to about 60° C., the compound of formula 13 is generated in which the following configuration of the epoxide moiety may predominate:

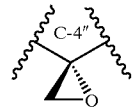

In step 1 of Scheme 3B, the compound of formula 13 may be converted to a compound of formula 14 wherein $R_{10}$ is hydroxy and $R_{19}$ is a group that is attached to the C4" carbon through a methylene group, such as where $R_{19}$, is $-CH_2NR^6R^8$ or $-CH_2S(O)_nR^8$ wherein n, $R^6$, and $R^8$ are as defined above. To prepare a compound of formula 14 wherein $R^{19}$ is $-CH_2NR^6R^8$, the compound of formula 13 may be treated with a compound of formula $HNR^6R^8$, wherein $R^6$ and $R^8$ are as defined above, in the absence or presence of a solvent such as water, methanol, or THF, or a mixture of the foregoing solvents, at a temperature ranging from about room temperature to about 100° C., preferably 60° C., optionally in the presence of a metal halide such as potassium iodide, pyridinium hydrochloride, or tetraalkylammonium halide reagent such as benzene or toluene at a temperature ranging from about room temperature to about 120° C.

The compounds of scheme 4 can be prepared using substantially the same methods described in U.S. Pat. No. 3,681,322, issued Aug. 1, 1972 and methods known to one skilled in the art.

In step 1 of Scheme 4, the C-9 carbonyl, of formula 15, is converted to the corresponding oxime at the C9 position by reacting the macrolide with hydroxylamine or preferably, a hydroxylamine salt such as a hydrochloride. Under presently preferred conditions, at least one molar equivalent, usually an excess, 5–10 equivalents, is usually employed in a weakly basic, tertiary amine (preferably pyridine) as a solvent; at a temperature range 20–80° C. A protic solvent, such as methanol, can also be used in conjunction with a base, such as barium carbonate, to provide a weakly basic solvent.

In stop 2 of Scheme 4, the oxime of formula 16 may be reduced to the corresponding imine by treating with a metal halide such at $TiCl_3$ in an acetate buffered solvent such as methanol or ethanol, methanol preferred. Reduction is also possible with divalent vanadium (prepared by Zn/Hg/HCl reduction of vanadyl sulphate) in a protic organic solvent such as methanol or ethanol, methanol preferred.

In step 3 of Scheme 4, the imine of formula 17 may be reduced to the corresponding amine, of formula 18, by various methods familiar to those skilled in the art. A preferred method incorporates the use of boron reducing reagents such as sodium borohydride, generally used in excess, 2–10 equivalents, in protic solvents such as methanol or ethylene glycol, at a temperature range of –5–40° C., preferably 0–20° C.

The compounds of the present invention may have asymmetric carbon atoms and therefore exist in different enantiomeric and diastereomeric forms Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness In the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes 2 transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibaterial assay is performed in microtiter trays and Interpreted according to *Performance Standards for Antimicrobial Disk Susceptibility Tests—Sixth Edition; Approved Standard,* published by The National Committee for Clinical Laboratory Standards (NCCLS) guidelines: the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphyloccccus aureus* 1120 | ermC |
| *Staphyloccccus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | mefA |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Haemophilus influenzae* 0085 | susceptible; acr AB-like |
| *Haemophilus influenzae* 0131 | susceptible; acr AB-like |
| *Moraxella catarrhalis* 0040 | susceptible |
| *Moraxella catarrhalis* 1055 | erythromycin intermediate resistance |
| *Escherichia coli* 0266 | susceptible; acr AB |
| *Haemophilus influenzae* 1100 | susceptible: acr AB-like |

Assay II is utilized to test for activity against *Pasteurella multocida* and Assay III is utilized to test for activity against *Pasteurella haemolytica.*

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/mi to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1×challenge dose; a 10×challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula 1, 11, 8 and 9 and the pharmaceutically acceptable salt thereof (hereinafter "the active compounds"), may be adminstered through oral, parenteral, topical, or rectal routes in the treatment of bacterial and protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, herd candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

The compounds of Examples 1 to 9 have the general formula depicted with the R substituents indicated in the Tables below. The compounds were prepared as described in the Preparations described below. In the Tables, the yield and mass spectra ("Mass Spec") data apply to the final product.

TABLE 1

| Example | R$^1$ Substituent | R$^2$ Substituent | Preparation | % Yield | Mass Spec. |
|---|---|---|---|---|---|
| 1-1 | isopropyl | H | 1 | 95 | 747 |
| 1-2 | cyclopropyl | H | 1 | 96 | 745 |
| 1-3 | sec-butyl | H | 1 | 95 | 761 |
| 1-4 | cyclobutyl | H | 1 | 98 | 759 |
| 1-5 | cyclopentyl | H | 1 | 94 | 773 |
| 1-6 | methylthioethyl | H | 1 | 91 | 779 |
| 1-7 | cyclopropyl | OH | 1 | 95 | 761 |
| 1-8 | cyclobutyl | OH | 1 | 86 | 775 |

Preparation 1

An amount of 0.095–4.96 g of the corresponding macrolide of formula 1 was dissolved in 1.9–50 mL of anhydrous pyridine. Hydroxylamine hydrochloride (7.5 equiv.) was added and the solution heated to 60° C. and stirred for 24 hours. The reaction was worked up by decanting into 50 mL of a 1:1 mixture of methylene chloride and water. The pH of the reaction mixture was adjusted to 9–11 using 1N NaOH, the reaction mixture was extracted 3×25 mL methylene chloride, and dried over Na$_2$SO$_4$. Filtration and concentration of filtrate yielded a light yellow solid product. The product was carried on to the next step without further purification.

PREPARATION FOR EXAMPLE 1-1

(Table 1)

400 mg of the corresponding macrolide of formula 1, where R$^1$ is isopropyl and R$^2$ is H, was dissolved in 8 mL of anhydrous pyridine. Hydroxylamine hydrochloride (0.285 g, 7.5 equiv.) was added and the solution heated to 60° C. and stirred for 24 hours. The reaction was worked up by decanting into 50 mL of a 1:1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.403 g) was carried on to the next step without further purification.

PREPARATION FOR EXAMPLE 1-2
(Table 1)

250 mg of the corresponding macrolide of formula 1, where $R^1$ is cyclopropyl and $R^2$ is H, was dissolved in 5 mL of anhydrous pyridine. Hydroxylamine hydrochloride (0.178 g, 7.5 equiv.) was added and the solution heated to 60° C. and stirred for 24 hours. The reaction was worked up by decanting into 50 mL of a 1:1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.252 g) was carried on to the next step without further purification.

PREPARATION FOR EXAMPLE 1-3
(Table 1)

250 mg of the corresponding macrolide of formula 1, where $R^1$ is sec-butyl and $R^2$ is H, was dissolved in 5 mL of anhydrous pyridine. Hydroxylamine hydrochloride (0.175 g, 7.5 equiv.) was added and the solution heated to 60° C. and stirred for 24 hours. The reaction was worked up by decanting into 60 mL of a 1:1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.249 g) was carried on to the next step without further purification.

PREPARATION FOR EXAMPLE 1-4
(Table 1)

250 mg of the corresponding macrolide of formula 1, where $R^1$ is cyclobutyl and $R^2$ is H, was dissolved in 5 mL of anhydrous pyridine. Hydroxylamine hydrochloride (0.175 g, 7.5 equiv.) was added and the solution heated to 60° C. and stirred for 24 hours. The reaction was worked up by decanting into 50 mL of a 1:1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.249 g) was carried on to the next step without further purification.

PREPARATION FOR EXAMPLE 1-5
(Table 1)

100 mg of the corresponding macrolide of formula 1, where $R^1$ is cyclopentyl and $R^2$ is H, was dissolved in 2 mL of anhydrous pyridine. Hydroxylamine hydrochloride (0.070 g, 7.5 equiv.) was added and the solution heated to 60° C. and stirred for 24 hours. The reaction was worked up by decanting into 50 mL of a 1:1 mixture of methylene chloride and water. The pH was adjusted to 9–11 using 1N NaOH, extracted 3×25 mL methylene chloride, and dried over $Na_2SO_4$. Filtration and concentration of filtrate yielded a light yellow solid product. The product (0.094 g) was carried on to the next step without further purification.

PREPARATION FOR EXAMPLE 1-6
(Table 1)

95 mg of the corresponding macrolide of formula 1, where $R^1$ is methylthioethyl and $R^2$ is H, was dissolved in 1.9 mL of anhydrous pyridine. Hydroxylamine hydrochloride (0.065 g, 7.5 equiv.) was added and the solution heated to 60° C. and stirred for 24 hours. The reaction was worked up by decanting into 50 mL of a 1.1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.091 g) was carried on to the next step without further purification.

PREPARATION FOR EXAMPLE 1-7
(Table 1)

98 mg of the corresponding macrolide of formula 1, where $R^1$ is cyclopropyl and $R^2$ is OH, was dissolved in 2.0 mL of anhydrous pyridine. Hydroxylamine hydrochloride (0.068 g, 7.5 equiv.) was added and the solution heated to 60° C. and stirred for 24 hours. The reaction was worked up by decanting into 50 mL of a 1:1 mixture of methylene chloride and water. The pH was adjusted to 9 using 1N NaOH, extracted 3×25 mL methylene chloride, and dried over $Na_2SO_4$. Filtration and concentration of filtrate yielded a light yellow solid product. The product (0.100 g) was carried on to the next step without further purification.

PREPARATION FOR EXAMPLE 1-8
(Table 1)

4.96 g of the corresponding macrolide of formula 1, where $R^1$ is cyclobutyl and $R^2$ is OH, was dissolved in 50.0 mL of anhydrous pyridine. Hydroxylamine hydrochloride (3.4 g. 7.5 equiv.) was added and the solution heated to 60° C. and stirred for 24 hours. The reaction was worked up by decanting into 50 mL of a 1:1 mixture of methylene chloride and water. The pH was adjusted to 9 using 1N NaOH, extracted 3–25 mL methylene chloride, and dried over $Na_2SO_4$. Filtration and concentration of filtrate yielded a light yellow solid product. The product (4.24 g) was carried on to the next step without further purification.

TABLE 2

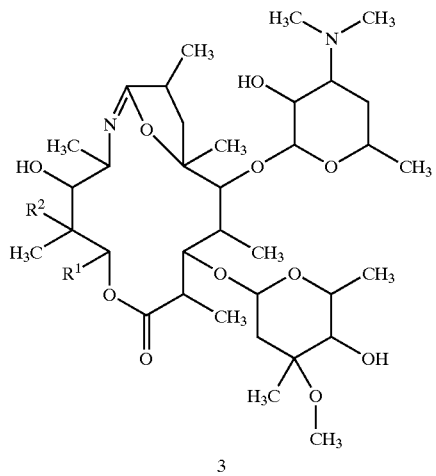

| Example | $R^1$ Substituent | $R^2$ Substituent | Preparation | % Yield | Mass Spec. |
|---|---|---|---|---|---|
| 2-1 | isopropyl | H | 2 | 81 | 729 |
| 2-2 | cyclopropyl | H | 2 | 90 | 727 |
| 2-3 | sec-butyl | H | 2 | 85 | 743 |
| 2-4 | cyclobutyl | H | 2 | 98 | 741 |
| 2-5 | cyclopentyl | H | 2 | 41 | 755 |
| 2-6 | methylthioethyl | H | 2 | 28 | 761 |
| 2-7 | cyclopropyl | OH | 2 | 95 | 743 |
| 2-8 | cyclobutyl | OH | 2 | 97 | 747 |

Preparation 2

An amount of 60–500 mg of the corresponding oxime of formula 2 was dissolved in 1–7 mL of acetone. A 0.1 M aqueous solution of Na$_2$HCO$_3$ (2 equiv.) was added and the resulting mixture was cooled to 0–5° C. A 0.1 M solution of para-toluenesulfonyl chloride in acetone, cooled to 0–5° C., was added and the mixture stirred overnight. The reaction was worked up by decanting into 25 mL of a 1:1 mixture of methylene chloride and water. The pH of the reaction mixture was adjusted to 9–10 using 1N NaOH, the reaction mixture was extracted with 3×20 mL methylene chloride, and dried over Na$_2$SO$_4$. Filtration, concentration of filtrate yielded a solid product. The product was carried on to the next step without further purification. mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.485 g) was carried on to the next step without further purification.

PREPARATION FOR EXAMPLE 2-5

(Table 2)

84 mg of the corresponding oxime of formula 2, where R$^1$ is cyclopentyl and R$^2$ is H, was dissolved in 1 mL of acetone. A 0.1 M aqueous solution of Na$_2$HCO$_3$ (0.038 g in 0.5 mL water) was added and the resulting mixture was cooled to 0° C. A solution of para-toluenesulfonyl chloride (0.043 g) in acetone (0.5 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.042 g) was carried on to the next step without further purification.

PREPARATION FOR EXAMPLE 2-6

(Table 2)

85 mg of the corresponding oxime of formula 2, where R$^1$ is methylthioethyl and R$^2$ is H, was dissolved in 1 mL of acetone. A 0.1 M aqueous solution of Na$_2$HCO$_3$ (0.038 g in 0.5 mL water) was added and the resulting mixture was cooled to 0° C. A solution of para-toluenesulfonyl chloride (0.043 g) in acetone (0.5 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.024 g) was carried on to the next step without further purification.

PREPARATION FOR EXAMPLE 2-7

(Table 2)

60 mg of the corresponding oxime of formula 2, where R$^1$ is cyclopropyl and R$^2$ is OH, was dissolved in 1 mL of acetone. A 0.1 M aqueous solution of Na$_2$HCO$_3$ (0.027 g in 0.5 mL water) was added and the resulting mixture was cooled to 0° C. A solution of para-toluenesulfonyl chloride (0.031 g) in acetone (0.5 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.058 g) was carried on to the next step without further purification.

PREPARATION FOR EXAMPLE 2-1

(Table 2)

415 mg of the corresponding oxime of formula 2, where R$^1$ is isopropyl and R$^2$ is H, was dissolved in 7 mL of acetone. A 0.1 M aqueous solution of Na$_2$HCO$_3$ (0.193 g in 2.0 mL water) was added and the resulting mixture was cooled to 0° C. A solution of para-toluenesulfonyl chloride (0.220 g) in acetone (2.0 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.329 g) was carried on to the next step without further purification.

PREPARATION FOR EXAMPLE 2-2

(Table 2)

200 mg of the corresponding oxime of formula 2, where R$^1$ is isopropyl and R$^2$ is H, was dissolved in 2 mL of acetone. A 0.1 M aqueous solution of Na$_2$HCO$_3$ (0.093 g in 1.0 mL water) was added and the resulting mixture was cooled to 0° C. A solution of para-toluenesulfonyl chloride (0.106 g) in acetone (1.0 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.177 g) was carried on to the next step without further purification.

PREPARATION FOR EXAMPLE 2-3

(Table 2)

420 mg of the corresponding oxime of formula 2, where R$^1$ is sec-butyl and R$^2$ is H, was dissolved in 7 mL of acetone. A 0.1 M aqueous solution of Na$_2$HCO$_3$ (0.192 g in 2.0 mL water) was added and the resulting mixture was cooled to 0° C. A solution of para-toluenesulfonyl chloride (0.220 g) in acetone (2.2 mL), cooled to 0° C., was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.348 g) was carried on to the next step without further purification.

PREPARATION FOR EXAMPLE 2-4

(Table 2)

500 mg of the corresponding oxime of formula 2, where R$^1$ is cyclobutyl and R$^2$ is H, was dissolved in 5 mL of acetone. A 0.1 M aqueous solution of Na$_2$HCO$_3$ (0.229 g in 2.0 mL water) was added and the resulting mixture was cooled to 0° C. A solution of para-toluenesulfonyl chloride (0.260 g) in acetone (2.0 mL), cooled to 0° C., was added and the mixture stirred overnight. The reaction was worked up by decanting into 25 mL of a 1:1

PREPARATION FOR EXAMPLE 2-8

(Table 2)

500 mg of the corresponding oxime of formula 2, where R$^1$ is cyclobutyl and R$^2$ is OH, was dissolved in 5 mL of acetone. A 0.1 M aqueous solution of Na$_2$HCO$_3$ (0.224 g in 2.5 mL water) was added and the resulting mixture was cooled to 0° C. A solution of para-toluenesulfonyl chloride (0.255 g) in acetone (2.5 mL), cooled to 0° C,. was added and the mixture stirred overnight. The reaction was worked up by decanting into 25 mL of a 1:1 mixture of methylene chloride and water. The pH was adjusted to 9 using 1N NaOH, extracted with 3×20 mL methylene chloride, and dried over Na$_2$SO$_4$. Filtration, concentration of filtrate yielded a solid product. The product (0.485 g) was carried on to the next step without further purification.

TABLE 3

[Structure of compound 5 with R¹ and R² substituents]

| Example | R¹ Substituent | R² Substituent | Preparation | % Yield | Mass Spec. |
|---------|----------------|----------------|-------------|---------|------------|
| 3-1 | isopropyl | H | 4 | 93 | 733 |
| 3-2 | cyclopropyl | H | 3 | 10 | 731 |
| 3-3 | sec-butyl | H | 4 | 45 | 747 |
| 3-4 | cyclobutyl | H | 4 | 84 | 745 |
| 3-5 | cyclopentyl | H | 3 | 88 | 759 |
| 3-6 | cyclopropyl | OH | 4 | 92 | 747 |
| 3-7 | cyclobutyl | OH | 4 | 90 | 761 |

Preparation 3

An amount of 42–165 mg of the corresponding imidate of formula 3 was dissolved in glacial acetic acid. Platinum oxide catalyst (50 mole %) was added, the reaction flushed with nitrogen, placed under 50 psi hydrogen and shaken at room temperature for 24 hours. Additional platinum oxide catalyst (60 mole %) was added, the reaction flushed with nitrogen, placed under 50 psi hydrogen and shaken at room temperature for additional 24–48 hours. The reaction was worked up by filtration through Celite™. 25 mL of water was added and the pH of the reaction mixture adjusted to 9–10 using 1N NaOH, the reaction mixture was extracted 3×25 mL methylene chloride, and dried over $Na_2SO_4$. Filtration and concentration of the filtrate yielded a solid product mixture containing azalide of formula 4 and lactam of formula 5. Isolation was accomplished by preparative HPLC.

Preparation 4

An amount of 11–260 mg of the corresponding imidate of formula 3 was dissolved in THF and ethylene glycol then cooled to 0–5° C. $NaBH_4$ (5–10 equiv.) was added and the reaction stirred for 4 hours at 0–5° C. and then warmed to room temperature. The reaction was worked up by decanting into 10 mL of a 1:1 mixture of methylene chloride and water. The aqueous was re-extracted 3–5 mL methylene chloride. The organic layers were combined and dried over $Na_2SO_4$. Filtration and concentration yielded a solid product.

PREPARATION FOR EXAMPLE 3-1
(Table 3)

150 mg of the corresponding imidate of formula 3, where R¹ is isopropyl and R² is H, was dissolved in 3.75 mL tetrahydrofuran and 7.5 mL ethylene glycol and then cooled to 0–5° C. $NaBH_4$ (0.039 g) was added and the reaction stirred for 6 hours at 0–5° C. and then warmed to room temperature. The reaction was worked up by decanting into 10 mL of a 1:1 mixture of methylene chloride and water. The aqueous was reextracted 3×5 mL methylene chloride. The organic layers were combined and dried over $Na_2SO_4$. Filtration and concentration yielded a solid product (0.149 g).

PREPARATION FOR EXAMPLE 3-2
(Table 3)

165 mg of the corresponding imidate of formula 3, where R¹ is cyclopropyl and R² is H, was dissolved in glacial acetic acid (20 mL). Platinum oxide catalyst (0.028 g, 50 mole %) was added, the reaction flushed with nitrogen, placed under 50 psi hydrogen and shaken at room temperature for 24 hours. Additional platinum oxide catalyst (50 mole %) was added, the reaction flushed with nitrogen, placed under 50 psi hydrogen and shaken at room temperature for additional 24 hours. Reaction was worked up by filtration through Celite™. 25 mL of water was added and the pH adjusted to 9 using 1N NaOH, extracted 3×25 mL methylene chloride, and dried over $Na_2SO_4$. Filtration and concentration of the filtrate yielded a solid product mixture containing azalide of formula 4 and lactam of formula 5. Isolation was accomplished by preparative HPLC (0.019 g).

PREPARATION FOR EXAMPLE 3-3
(Table 3)

11 mg of the corresponding imidate of formula 3, where R¹ sec-butyl and R² is H, was dissolved in 0.275 mL tetrahydrofuran and 0.55 mL ethylene glycol and then cooled to 0–5° C. $NaBH_4$ (0.003 g) was added and the reaction stirred for 6 hours at 0–5° C. and then warmed to room temperature. The reaction was worked up by decanting into 10 mL of a 1:1 mixture of methylene chloride and water. The aqueous was re-extracted 3×5 mL methylene chloride. The organic layers were combined and dried over $Na_2SO_4$. Filtration and concentration yielded a solid product (0.005 g).

PREPARATION FOR EXAMPLE 3-4
(Table 3)

250 mg of the corresponding imidate of formula 3, where R¹ cyclobutyl and R² is H, was dissolved in 3.83 mL tetrahydrofuran and 5.0 mL ethylene glycol and then cooled to 0–5° C. $NaBH_4$ (0.191 g) was added and the reaction stirred for 6 hours at 0–5° C. and then warmed to room temperature. The reaction was worked up by decanting into 10 mL of a 1:1 mixture of methylene chloride and water. The aqueous was re-extracted 3×5 mL methylene chloride. The organic layers were combined and dried over $Na_2SO_4$. Filtration and concentration yielded a solid product (0.201 g).

PREPARATION FOR EXAMPLE 3-5
(Table 3)

42 mg of the corresponding imidate of formula 3, there R¹ is cyclopentyl and R² is H, was dissolved in glacial acetic acid (10 mL). Platinum oxide catalyst (0.006 g, 50 mole %) was added, the reaction flushed with nitrogen, placed under 50 psi hydrogen and shaken at room temperature for 24 hours. Additional platinum oxide catalyst (50 mole %) was added, the reaction flushed with nitrogen, placed under 50 psi hydrogen and shaken at room temperature for additional 24 hours. Reaction was worked up by filtration through Celite™. 25 mL of water was added and the pH adjusted to 9 using 1N NaOH, extracted 3×25 mL methylene chloride, and dried over $Na_2SO_4$. Filtration and concentration of the filtrate yielded a solid product mixture containing azalide of formula 4 and lactam of formula 5. Isolation was accomplished by preparative HPLC (0.037 g).

PREPARATION FOR EXAMPLE 3-8
(Table 3)

60 mg of the corresponding imidate of formula 3, where $R^1$ cyclopropyl and $R^2$ is OH, was dissolved in 0.6 mL tetrahydrofuran and 1.8 mL ethylene glycol and then cooled to 0–5° C. $NaBH_4$ (0.046 g) was added and the reaction stirred for 6 hours at 0–5° C. and then warmed to room temperature. The reaction was worked up by decanting into 10 mL of a 1:1 mixture of methylene chloride and water. The aqueous was re-extracted 3×5 mL methylene chloride. The organic layers were combined and dried over $Na_2SO_4$. Filteration and concentration yielded a solid product (0.055 g).

PREPARATION FOR EXAMPLE 3-7
(Table 3)

250 mg of the corresponding imidate of formula 3, where $R^1$ cyclobutyl and $R^2$ is OH, was dissolved in 3.75 mL tetrahydrofuran and 5.0 mL ethylene glycol and then cooled to 0–5° C. $NaBH_4$ (0.187 g) was added and the reaction stirred for 6 hours at 0–5° C. and then warmed to room temperature. The reaction was worked up by decanting into 10 mL of a 1:1 mixture of methylene chloride and water. The aqueous was re-extracted 3×5 mL methylene chloride. The organic layers were combined and dried over $Na_2SO_4$. Filteration and concentration yielded a solid product (0.226 g).

The nmr data for compounds included within those of formula 5 is shown in Tables 3A and 3B below.

TABLE 3A

| Carbon # | $^{13}$C-ppm | $^1$H-ppm |
|---|---|---|
| 1 | 178.89 | — |
| 2 | 45.92 | 2.84 |
| 3 | 78.39 | 4.37 |
| 4 | 42.58 | 1.98 |
| 5 | 84.03 | 3.69 |
| 6 | 74.48 | — |
| 7 | 42.78 | 1.80 |
|   |       | 1.42 |
| 8 | 29.84 | 1.87 |
| 9 | 57.55 | 3.14 |
|   |       | 1.95 |
| 10 | 57.42 | 2.68 |

TABLE 3A-continued

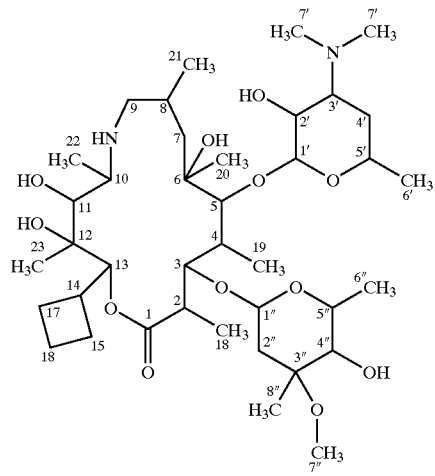

| Carbon # | $^{13}$C-ppm | $^1$H-ppm |
|---|---|---|
| 11 | 73.24 | 3.50 |
| 12 | 75.25 | — |
| 13 | 78.48 | 4.87 |
| 14 | 34.91 | 2.89 |
| 15 | 25.84 | 2.01 |
|   |       | 1.95 |
| 16 | 19.64 | 1.92 |
|   |       | 1.76 |
| 17 | 26.90 | 2.04 |
|   |       | 1.91 |
| 18 | 15.68 | 1.28 |
| 19 | 9.69 | 1.12 |
| 20 | 27.58 | 1.37 |
| 21 | 22.48 | 1.02 |
| 22 | 14.18 | 1.24 |
| 23 | 17.30 | 1.10 |
| 24 | — | — |
| 1' | 103.51 | 4.49 |
| 2' | 71.27 | 3.30 |
| 3' | 66.21 | 2.54 |
| 4' | 29.36 | 1.75 |
|   |       | 1.30 |
| 5' | 69.24 | 3.57 |
| 6' | 21.79 | 1.28 |
| 7' | 40.84 | 2.37 |
| 1" | 95.52 | 5.14 |
| 2" | 35.24 | 2.40 |
|   |       | 1.64 |
| 3" | 73.39 | — |
| 4" | 78.55 | 3.10 |
| 5" | 68.05 | 4.13 |
| 6" | 18.73 | 1.38 |
| 7" | 49.91 | 3.40 |
| 8" | 22.04 | 1.30 |

TABLE 3B

| Carbon # | $^{13}$C-ppm | $^1$H-ppm |
|---|---|---|
| 1 | 178.71 | — |
| 2 | 45.77 | 2.84 |
| 3 | 79.20 | 4.31 |
| 4 | 42.04 | 2.05 |
| 5 | 84.33 | 3.70 |
| 6 | 74.49 | — |
| 7 | 42.82 | 1.77 |
|  |  | 1.43 |
| 8 | 30.13 | 1.86 |
| 9 | 57.57 | 3.11 |
|  |  | 1.99 |
| 10 | 57.49 | 2.59 |
| 11 | 73.92 | 3.31 |
| 12 | 38.60 | 1.64 |
| 13 | 79.07 | 5.12 |
| 14 | 41.71 | 2.16 |
| 15 | 28.90 | 1.70 |
|  |  | 1.20 |
| 16 | 25.67 | 1.69 |
|  |  | 1.55 |
| 17 | 25.49 | 1.69 |
|  |  | 1.54 |
| 18 | 31.10 | 1.74 |
|  |  | 1.27 |
| 19 | 15.75 | 1.25 |
| 20 | 9.72 | 1.10 |
| 21 | 27.62 | 1.36 |
| 22 | 22.49 | 1.00 |
| 23 | 12.79 | 1.11 |
| 24 | 9.81 | 0.86 |
| 1' | 103.50 | 4.50 |
| 2' | 71.41 | 3.28 |
| 3' | 66.05 | 2.52 |
| 4' | 29.40 | 1.71 |
|  |  | 1.28 |
| 5' | 69.15 | 3.56 |
| 6' | 21.81 | 1.27 |
| 7' | 40.81 | 2.34 |
| 1" | 95.81 | 5.09 |
| 2" | 35.37 | 2.38 |
|  |  | 1.61 |
| 3" | 73.41 | — |
| 4" | 78.54 | 3.07 |
| 5" | 66.05 | 4.10 |
| 6" | 18.75 | 1.36 |
| 7" | 49.86 | 3.37 |
| 8" | 22.04 | 1.28 |

TABLE 4

| Example | $R^1$ Substituent | $R^2$ Substituent | Preparation | % Yield | Mass Spec. |
|---|---|---|---|---|---|
| 4-1 | isopropyl | H | 5 | 92 | 747 |
| 4-2 | cyclopropyl | OH | 5 | 95 | 761 |

Preparation 5

The corresponding azalide of formula 5 was dissolved in chloroform. 37% formaldehyde (3.0 equiv.) and formic acid (3.0 equiv.) was added and the solution stirred at 45–50° C. for 12–24 hours. The reaction mixture was then concentrated under vacuum. The residue was then dissolved in 1–2 mL of methylene chloride. 2–5 mL of a saturated NaHCO$_3$ aqueous solution was then added. The layers were separated and the aqueous re-extracted with an equal volume of methylene chloride. The organics were combined and dried over Na$_2$SO$_4$. Filtered, concentrated, and isolated a solid.

PREPARATION FOR EXAMPLE 4-1
(Table 4)

25 mg of the corresponding azalide of formula 5, where $R^1$ is isopropyl and $R^2$ is H, was dissolved in 1.0 mL chloroform. 37% formaldehyde (7.5 microliter, 3.0 equiv.) and formic acid (10.5 microliter, 3.0 equiv.) was added and the solution stirred at 45–50° C. for 24 hours. The reaction mixture was then concentrated under vacuum. The residue was then dissolved in 2 mL of methylene chloride. 5.0 mL of a saturated NaHCO$_3$ aqueous solution was then added. The layers were separated and the aqueous re-extracted with an equal volume of methylene chloride. The organics were combined and dried over Na$_2$SO$_4$. Filtered, concentrated, and isolated a solid (0.023 g).

PREPARATION FOR EXAMPLE 4-2
(Table 4)

20 mg of the corresponding azalide of formula 5, where $R^1$ is cyclopropyl and $R^2$ is OH, was dissolved in 2.0 mL chloroform. 37% formaldehyde (6 microliter, 3.0 equiv.) and formic acid (8.5 microliter, 3.0 equiv.) was added and the solution stirred at 45–50° C. for 12 hours. The reaction mixture was then concentrated under vacuum. The residue was then dissolved in 2 mL of methylene chloride. 5.0 mL of a saturated NaHCO$_3$ aqueous solution was then added. The layers were separated and the aqueous re-extracted with an equal volume of methylene chloride. The organics were combined and dried over Na$_2$SO$_4$. Filtered, concentrated, and isolated a solid (0.019 g).

TABLE 5

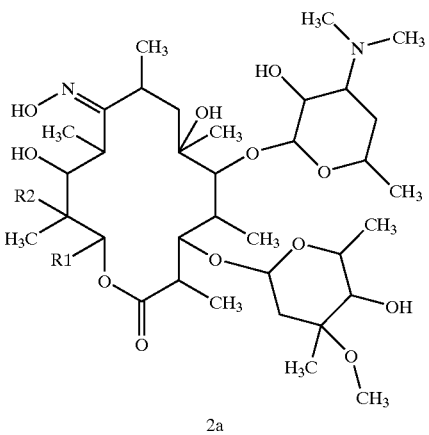

2a

| Example | R¹ Substituent | R² Substituent | Preparation |
|---|---|---|---|
| 1 | isopropyl | H | 6 |
| 2 | cyclopropyl | H | 6 |
| 3 | sec-butyl | H | 6 |
| 4 | cyclobutyl | H | 6 |
| 5 | cyclopentyl | H | 6 |
| 6 | methylthioethyl | H | 6 |
| 7 | furyl | H | 6 |
| 8 | cyclopropyl | OH | 6 |
| 9 | cyclobutyl | OH | 6 |

Preparation 6

The corresponding oxime of formula 2 is dissolved in ethanol. Lithium hydroxide monohydrate (2 equivalents) is added and the reaction mixture stirred overnight at room temperature. The reaction is concentrated under vacuum and partitioned between brine and ethyl acetate, the pH of the reaction mixture is adjusted to 9–10, the reaction mixture is extracted with ethyl acetate, and dried over $Na_2SO_4$. A 4:1 ratio of Z:E isomers is produced. Isolation of isomers is accomplished by either silica chromatography or crystallization from nitromethane.

TABLE 6

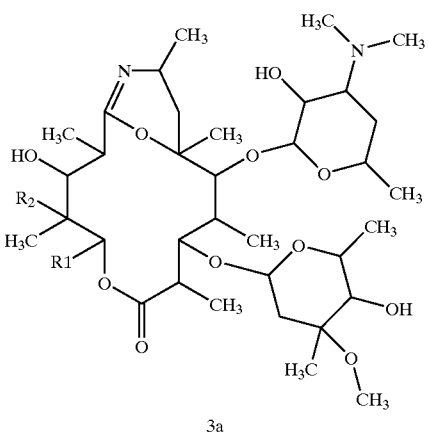

3a

| Example | R¹ Substituent | R² Substituent | Preparation |
|---|---|---|---|
| 1 | isopropyl | H | 7 |
| 2 | cyclopropyl | H | 7 |
| 3 | sec-butyl | H | 7 |

TABLE 6-continued

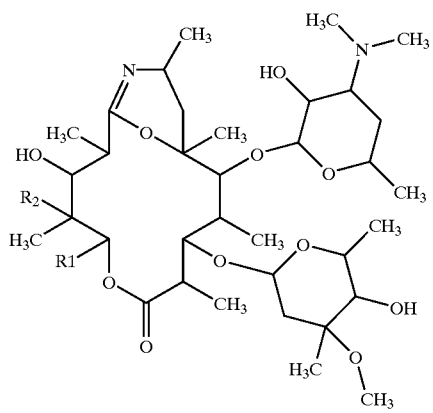

3a

| Example | R¹ Substituent | R² Substituent | Preparation |
|---|---|---|---|
| 4 | cyclobutyl | H | 7 |
| 5 | cyclopentyl | H | 7 |
| 6 | methylthioethyl | H | 7 |
| 7 | furyl | H | 7 |
| 8 | cyclopropyl | OH | 7 |
| 9 | cyclobutyl | OH | 7 |

Preparation 7

The corresponding oxime of formula 2a is dissolved in acetone. A 0.1 M aqueous solution of $Na_2HCO_3$ (2 equiv.) is added and the resulting mixture is cooled to 0–5° C. A 0.1 M solution of para-toluenesulfonyl chloride in acetone is added and the mixture stirred overnight. The reaction is worked up by decanting into 25 mL of a 1:1 mixture of methylene chloride and water. The pH of the reaction mixture is adjusted to 9–10 using 1N NaOH, the reaction mixture is extracted with 3–20 mL methylene chloride, and dried over $Na_2SO_4$. Filtration and concentration of filtrate yields a solid product. The product is carried on to the next step without further purification.

TABLE 7

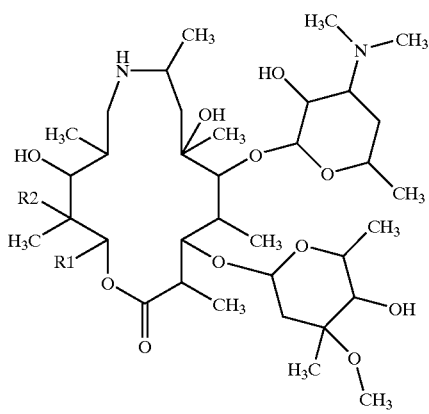

5a

| Example | R¹ Substituent | R² Substituent | Preparation |
|---|---|---|---|
| 1 | isopropyl | H | 8 |
| 2 | Cyclopropyl | H | 8 |
| 3 | sec-butyl | H | 8 |

TABLE 7-continued

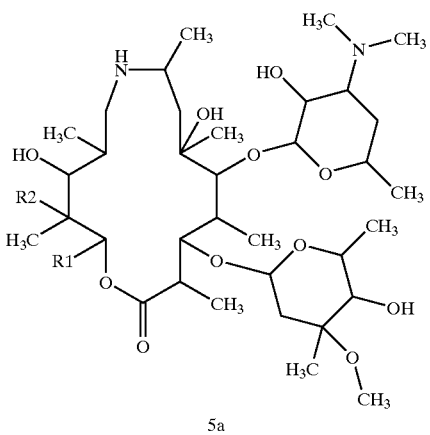

5a

| Example | R¹ Substituent | R² Substituent | Preparation |
|---------|----------------|----------------|-------------|
| 4 | Cyclobutyl | H | 8 |
| 5 | Cyclopentyl | H | 8 |
| 6 | Methylthioethyl | H | 8 |
| 7 | Furyl | H | 8 |
| 8 | Cyclopropyl | OH | 9 |
| 9 | Cyclobutyl | OH | 9 |

TABLE 8

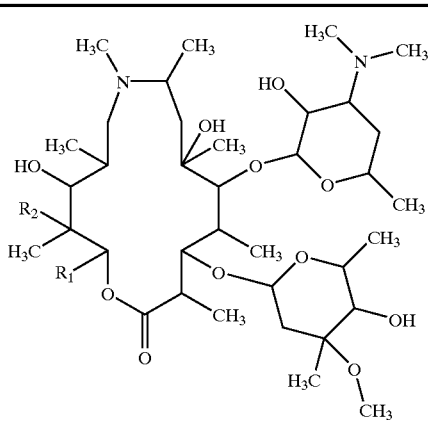

6a

| Example | R¹ Substituent | R² Substituent | Preparation |
|---------|----------------|----------------|-------------|
| 1 | isopropyl | H | 10 |
| 2 | cyclopropyl | H | 10 |
| 3 | sec-butyl | H | 10 |
| 4 | cyclobutyl | H | 10 |
| 5 | cyclopentyl | H | 10 |
| 6 | methylthioethyl | H | 10 |
| 7 | furyl | H | 10 |
| 8 | cyclopropyl | OH | 10 |
| 9 | cyclobutyl | OH | 10 |

Preparation 8

The corresponding imidate of formula 3a is dissolved in glacial acetic acid. Platinum oxide catalyst (50 mole %) is added, the reaction is flushed with nitrogen, placed under 50 psi hydrogen and shaken at room temperature for 24 hours. Additional platinum oxide catalyst (50 mole %) is added, the reaction is flushed with nitrogen, placed under 50 psi hydrogen and shaken at room temperature for additional 24–48 hours. The reaction is worked up by filtration through Celite™. A volume of 25 mL of water is added and the pH of the reaction mixture is adjusted to 9–10 using 1N NAOH, the reaction mixture is extracted 3×25 mL methylene chloride, and dried over $Na_2SO_4$. Filtration and concentration yields a solid product. Isolation is accomplished by HPLC.

Preparation 9

The corresponding imidate of formula 3a is dissolved in 0.5 mL MeOH and cooled to 0–5° C. $NaBH_4$ (10 equiv.) is added and the reaction stirred for 4 hours at 0–5° C., warmed to room temperature, and stirred overnight. The reaction is worked up by decanting into 10 mL of a 1:1 mixture of methylene chloride and water, the pH of the reaction mixture adjusted to 8–9 using 1N NaOH, extracted 3×5 mL methylene chloride, and dried over $Na_2SO_4$. Filtration and concentration yields a solid product. Purification is accomplished by HPLC.

Preparation 10

The corresponding azalide of formula 5a is dissolved in chloroform. 37% formaldehyde (1.0 equiv.) and formic acid (1.0 equiv.) is added and the solution stirred at 45–50° C. for 48–72 hours. The reaction mixture is then decanted into a 1:1 mixture of chloroform and water, the pH of the reaction mixture is adjusted to 9–10 using 1N NaOH, the reaction mixture is extracted with chloroform, and dried over $Na_2SO_4$. Filtration and concentration yields a solid product. Isolation of product is accomplished by either silica chromatography or HPLC.

Preparation 11

An amount of 100–200 mg of the corresponding azalide is dissolved in a solution of MeOH (5–10 mL) and acetyl chloride (2.6 equivalents). The resulting mixture is stirred overnight at room temperature, concentrated under vacuum, and then taken up in a small amount of MeOH (1 mL). The mixture is then heated, combined with hot cyclohexane (10 mL), and cooled to room temperature. The product is isolated by filtration.

What is claimed is:
1. A compound of the formula

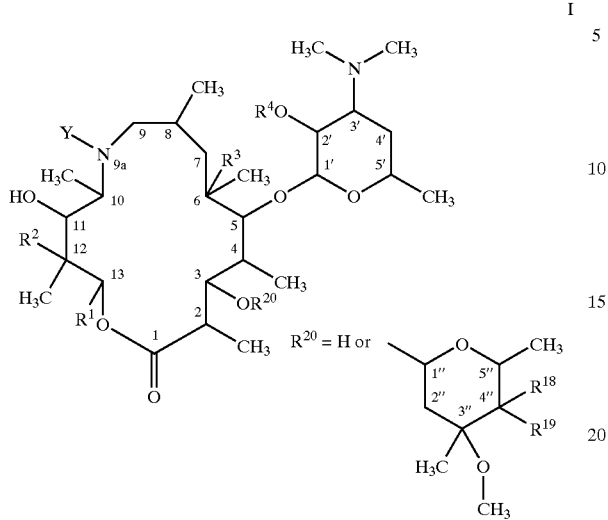

or a pharmaceutically acceptable salt thereof, wherein:

Y is H, $C_1$–$C_{10}$ alkyl, $C_2$–$C_{10}$ alkenyl, $C_2$–$C_{10}$ alkynyl, —$(CH_2)_m C_6$–$C_{10}$aryl, —$(CH_2)_m$(5–10 membered heteroaryl), wherein m is an integer ranging from 0 to 4, and wherein the alkyl, alkenyl, aryl, heteroaryl and alkynyl groups are optionally substituted by 1 to 3 substituents independently selected from halo, cyano, nitro, trifluoromethyl, azido, —C(O)$R^{21}$, —OC(O)$R^{21}$, —$NR^{21}$C(O)$R^{22}$, —C(O)$NR^{21}$ $R^{22}$, —$NR^{21}R^{22}$, hydroxy, $C_1$–$C_8$ alkyl, $C_1$–$C_6$ alkoxy, $C_8$–$C_{10}$ aryl, and 5–10 membered heteroaryl;

$R^1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ may be with a formula (a) as shown below:

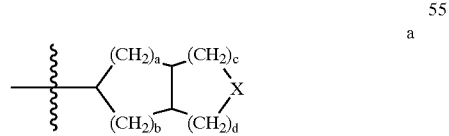

wherein X is O, S or —$CH_2$—, a, b, c, and d are each independently an integer ranging from 0 to 2 and a+b+c+d≦5;

or $R^1$ is $CH_2R^{24}$, wherein $R^{24}$ is H, $C_2$–$C_8$alkyl, $C_2$–$C_8$alkenyl, $C_2$–$C_8$alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$–$C_8$cycloalkyl or $C_5$–$C_8$cycloalkenyl either or which may be optionally substituted by methyl or one or more $C_1$–$C_4$alkyl groups or halo atoms; or a 3 to 6 membered oxygen or sulphur containing heterocyclic ring which may be saturated or fully or partially unsaturated and which may optionally be substituted by one or more $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one or more $C_1$–$C_4$alkyl groups or halo atoms;

$R^2$ is H or OH;

$R^3$ is H, OH, or $OCH_3$;

$R^4$ is H, —C(O)$R^9$, —C(O)$OR^9$, —C(O)$NR^9R^{10}$ or a hydroxy protecting group;

$R^5$ is —$SR^8$, —$(CH_2)_n$C(O)$R^8$ wherein n is 0 or 1, $C_1$–$C_{10}$ alkyl, $C_2$–$C_{10}$ alkenyl, $C_2$–$C_{10}$ alkynyl, —$(CH_2)_m$ ($C_6$–$C_{10}$ aryl), or —$(CH_2)_m$(5–10 membered heteroaryl), wherein m is an integer ranging from 0 to 4, and wherein the foregoing $R^5$ groups are optionally substituted by 1 to 3 $R^{16}$ groups;

each $R^6$ and $R^7$ is independently H, hydroxy, $C_1$–$C_6$ alkoxy, $C_1$–$C_6$ alkyl, $C_2$–$C_6$ alkenyl, $C_2$–$C_6$ alkynyl, —$(CH_2)_m$($C_6$–$C_{10}$ aryl), or —$(CH_2)_m$(5–10 membered heteroaryl), wherein m is an integer ranging from 0 to 4;

each $R^8$ is independently H, $C_1$–$C_{10}$ alkyl, $C_2$–$C_{10}$ alkenyl, $C_2$–$C_{10}$ alkynyl, —$(CH_2)_q CR^{11}R^{12}(CH_2)_r NR^{13}R^{14}$ wherein q and r are each independently an integer ranging from 0 to 3 except q and r are not both 0, —$(CH_2)_m$($C_6$–$C_{10}$ aryl), or —$(CH_2)_m$(5–10 membered heteroaryl), wherein m is an integer ranging from 0 to 4, and wherein the foregoing $R^8$ groups, except H, are optionally substituted by 1 to 3 $R^{16}$ groups;

or where $R^8$ is as —$CH_2NR^8R^{15}$, $R^{15}$ and $R^8$ may be taken together to form a 4–10 membered monocyclic or polycyclic saturated ring or a 5–10 membered heteroaryl ring, wherein said saturated and heteroaryl rings optionally include 1 or 2 heteroatoms selected from O, S and —N($R^8$)—, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{16}$ groups;

each $R^9$ and $R^{10}$ is independenily H or $C_1$–$C_6$alkyl;

each $R^{11}$, $R^{12}$, $R^{13}$ and $R^{14}$ is independently selected from H, $C_1$–$C_{10}$ alkyl —$(CH_2)_m$($C_6$–$C_{10}$ aryl), and —$(CH_2)_m$ (5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —$(CH_2)_p$— wherein p is an integer ranging from 0 to 3 such that a 4–7 membered saturated ring is formed that optionally includes 1 or 2 carbon-carbon double or triple bonds;

or $R^{13}$ and $R^{14}$ are taken together to form a 4–10 membered monocyclic or polycyclic saturated ring or a 5–10 membered heteroaryl ring, wherein said saturated and heteroaryl rings optionally include 1 or 2 heteroatoms selected from O, S and —$N(R^8)$—, in addition to the nitrogen to which $R^{13}$ and $R^{14}$ are attached, said saturated ring optionally includes 1 or 2 carbon-carbon double or triple bonds, and said saturated and heteroaryl rings are optionally substituted by 1 to 3 $R^{16}$ groups;

$R^{16}$ is H, $C_1$–$C_{10}$ alkyl, $C_2$–$C_{10}$ alkenyl, or $C_2$–$C_{10}$ alkynyl, wherein the foregoing $R^{16}$ groups are optionally substituted by 1 to 3 substituents independently selected from halo and —$OR^9$;

each $R^{16}$ is independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)NR^6R^7$, —$NR^6R^7$, hydroxy, $C_1$–$C_6$ alkyl, $C_1$–$C_6$ alkoxy, —$CH_2)_m(C_6$–$C_{10}$ aryl), and —$(CH_2)_m$(5–10 membered heteroaryl), wherein m is an integer ranging from 0 to 4, and wherein said aryl and heteroaryl substituents are optionally substituted by 1 or 2 substituents independently selected from halo, cyano, nitro, trifloromethyl, azido, —$C(O)R^{17}$, —$C(O)OR^{17}$, —$C(O)OR^{17}$, —$OC(O)OR^{17}$, —$NR^8C(O)R^7$, —$C(O)NR^6R^7$, —$NR^6R^7$, hydroxy, $C_1$–$C_6$ alkyl, and $C_1$–$C_6$ alkoxy;

each $R^{17}$ is independently selected from H, $C_1$–$C_{10}$ alkyl $C_2$–$C_{10}$ alkenyl, $C_2$–$C_{10}$ alkynyl, —$(CH_2)_m(C_6$–$C_{10}$ aryl), and —$CH_2)_m$(5–10 membered heteroaryl), wherein m is an integer ranging from 0 to 4, provided that $R^8$ is not H where $R^{19}$ is —$CH_2S(O)_nR^6$;

$R^{16}$ is OH;

$R^{15}$ is $C_1$–$C_{10}$ alkyl, $C_2$–$C_{10}$ alkenyl, $C_2$–$C_{10}$ alkynyl, cyano, —$CH_2S(O)_nR^8$ wherein n is an integer ranging from 0 to 2, —$CH_2OR^8$, —$CH_2N(OR^9)R^8$, —$CH_2NR^8R^{15}$, —$(C_2)_m(C_6$–$C_{10}$ aryl), or —$(CH_2)_m$(5–10 membered heteroaryl), wherein m is an integer ranging from 0 to 4, and wherein the foregoing $R^{19}$ groups are optionally substituted by 1 to 3 $R^{16}$ groups;

or $R^{18}$ and $R^{19}$ are taken together to form an oxazolyl ring as shown below

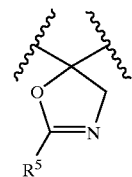

and;

each $R^{21}$ and $R^{22}$ is independently H, hydroxy, $C_1$–$C_6$ alkoxy, $C_1$–$C_6$ alkyl, $C_2$–$C_6$ alkenyl, $(CH_2)_m(C_5$–$C_{10})$ aryl, $(CH_2)_m$(5–10 membered heteroaryl), wherein m is an integer ranging from 0 to 4, or $C_2$–$C_{10}$ alkylyl.

2. The compound of formula of claim 1 wherein $R^{20}$ is

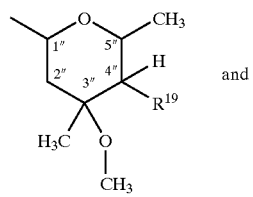

$R^1$ is isopropyl, $R^2$ is H and $R^{19}$ is OH;

$R^1$ is isopropyl, $R^2$ is OH and $R^{19}$ is OH;

$R^1$ is cyclopropyl, $R^2$ is H and $R^{19}$ is OH;

$R^1$ is cyclopropyl, $R^2$ is OH and $R^{19}$ is OH;

$R^1$ is sec-butyl, $R^2$ is H and $R^{19}$ is OH;

$R^1$ sec-butyl, $R^2$ is OH and $R^{19}$ is OH;

$R^1$ is cyclobutyl, $R^2$ is H and $R^{19}$ is OH;

$R^1$ is cyclobutyl, $R^2$ is OH and $R^{19}$ is OH;

$R^1$ is cyclopentyl, $R^2$ is H and $R^{19}$ is OH;

$R^1$ is cyclopentyl, $R^2$ is OH and $R^{19}$ is OH;

$R^1$ is methylthioethyl, $R^2$ is H and $R^{19}$ is OH;

$R^1$ is methylthioethyl, $R^2$ is OH and $R^{19}$ is OH;

$R^1$ is 3-furyl, $R^2$ is H and $R^{19}$ is OH; or $R^1$ is 3-furyl, $R^2$ is OH and $R^{19}$ is OH.

3. A pharmaceutical composition for the treatment of a bacterial infection or a protozoa infection in a mammal, fish or bird which comprises a therapeutically effective amount of a compound of claim 1 or 2 and pharmaceutically acceptable carrier.

4. A method of treating of a bacterial infection or a protozoa infection in a mammal, fish or bird which comprises administering to said mammal, fish or bird a therapeutically effective amount of a compound of claim 1 or 2.

5. A process for preparing a compound of the formula

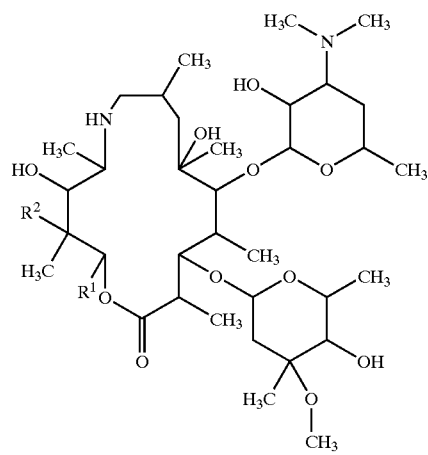

wherein $R^1$ and $R^2$ are as defined in claim 1, which comprises treating a compound of the formula

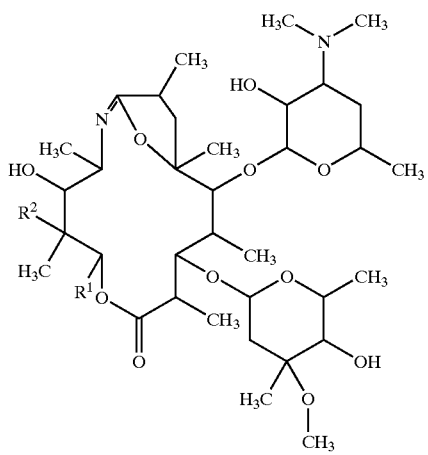

wherein $R^1$ and $R^2$ are as defined in claim 1, with a reducing agent.

6. The process of claim 5 wherein the reducing agent is $NaBH_4$ of platinum oxide.

7. A process for preparing a compound of the formula

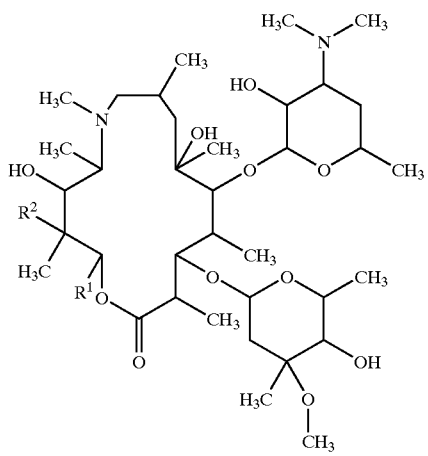

wherein $R^1$ and $R^2$ are as defined in claim 1, which comprises treating a compound of the formula

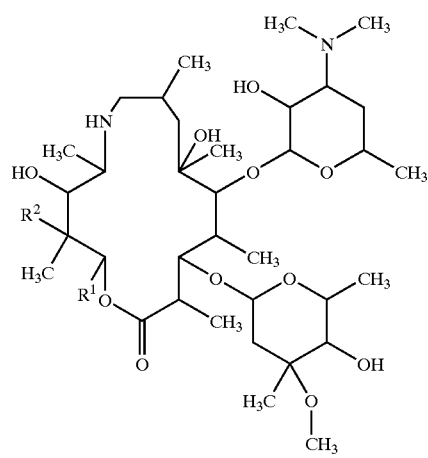

wherein $R^1$ and $R^2$ are as defined in claim 1, with a methylating agent.

8. The process of claim 7 wherein the methylating agent is formaldehyde.

9. A compound of the formula

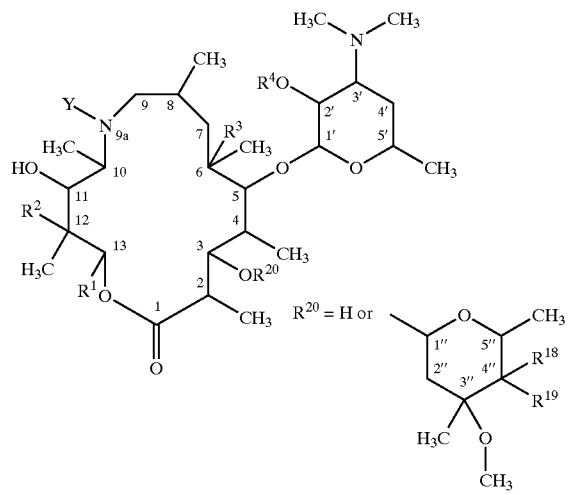

or a pharmaceutically acceptable salt thereof, wherein:

Y is H, $C_1$–$C_{10}$ alkyl, $C_2$–$C_{10}$ alkenyl, $C_2$–$C_{10}$ alkynyl, —$(CH_2)_m C_6$–$C_{10}$ aryl, —$(CH_2)_m$(5–10 membered heteroaryl), wherein m is an integer ranging from 0 to 4, and wherein the alkyl, alkenyl, aryl, heteroaryl and alkynyl groups are optionally substituted by 1 to 3 substituents independently selected from halo, cyano, nitro, trifluoromethyl, azido, —$C(O)R^{21}$, —$OC(O)R^{21}$, —$NR^2C(O)R^{22}$, —$C(O)NR^{21}R^{22}$, —$NR^{21}R^{22}$, hydroxy, $C_1$–$C_6$ alkyl, $C_1$–$C_6$ alkoxy, $C_6$–$C_{10}$ aryl, and 5–10 membered heteroaryl;

$R^1$ is an alpha-branched $C_3$–$C_8$ alkyl, alkenyl, alkynyl, alkoxyalkyl or alkylthioalkyl group any of which may optionally be substituted by one or more hydroxyl groups; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methyl or one or more hydroxyl or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms;

or $R^1$ is phenyl which may be optionally substituted with at least one substituent selected from $C_1$–$C_4$ alkyl, $C_1$–$C_4$ alkoxy and $C_1$–$C_4$ alkylthio groups, halogen atoms, hydroxyl groups, trifluoromethyl, and cyano;

or $R^1$ may be with a formula (a) as shown below:

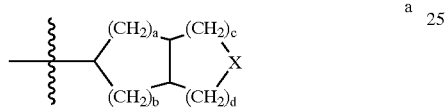

a wherein X is O, S or —$CH_2$—, a, b, c, and d are each independently an integer ranging from 0 to 2 and $a+b+c+d \leq 5$;

or $R^1$ is $CH_2R^{24}$, wherein $R^{24}$ is H, $C_2$–$C_8$alkyl, $C_2$–$C_8$alkenyl, $C_2$–$C_8$alkynyl, alkoxyalkyl or alkylthioalkyl containing from 1 to 6 carbon atoms in each alkyl or alkoxy group wherein any of said alkyl, alkoxy, alkenyl or alkynyl groups may be substituted by one or more hydroxyl groups or by one or more halo atoms; or a $C_3$–$C_8$cycloalkyl or $C_5$–$C_8$cycloalkenyl either or which may be optionally substituted by methyl or one or more $C_1$–$C_4$alkyl groups or halo atoms; or a 3 to 6 membered oxygen or sulphur containing heterocyclic ring which may be saturated or fully or partially unsaturated and which may optionally be substituted by one or more $C_1$–$C_4$alkyl groups or halo atoms; or a group of the formula $SR^{23}$ wherein $R^{23}$ is $C_1$–$C_8$alkyl, $C_2$–$C_8$alkenyl, $C_2$–$C_8$alkynyl, $C_3$–$C_8$cycloalkyl, $C_5$–$C_8$cycloalkenyl, phenyl or substituted phenyl wherein the substituent is $C_1$–$C_4$alkyl, $C_1$–$C_4$alkoxy or halo, or a 3 to 6 membered oxygen or sulphur-containing heterocyclic ring which may be saturated, or fully or partially unsaturated and which may optionally be substituted by one or more $C_1$–$C_4$alkyl groups or halo atoms;

$R^2$ is H or OH;

$R^3$ is H, OH, or $OCH_3$;

$R^4$ is H, —$C(O)R^9$, —$C(O)OR^9$, —$C(O)NR^9R_{10}$ or a hydroxy protecting group;

$R^5$ is —$SR^{23}$, —$(CH_2)_nC(O)R^{23}$ wherein n is 0 or 1, $C_1$–$C_{10}$ alkyl, $C_{2-C_{10}}$ alkenyl, $C_2$–$C_{10}$ alkynyl, —$(CH_2)_m(C_6$–$C_{10}$ aryl), or —$(CH_2)_m(5$–10 membered heteroaryl), wherein m is an integer ranging from 0 to 4, and wherein the foregoing $R^5$ groups are optionally substituted by 1 to 3 $R^{16}$ groups;

each $R^8$ and $R^7$ is independently H, hydroxy, $C_1$–$C_6$ alkoxy, $C_1$–$C_6$ alkyl, $C_2$–$C_6$ alkenyl, $C_2$–$C_6$ alkynyl, —$(CH_2)_m(C_6$–$C_{10}$ aryl), or —$(CH_2)_m(6$–10 membered heteroaryl), wherein m is an integer ranging from 0 to 4;

each $R^8$ is independently H, $C_1$–$C_{10}$ alkyl, $C_2$–$C_{10}$ alkenyl, $C_2$–$C_{10}$ alkynyl, —$(CH_2)_qCR^{11}R^{12}(CH_2)_r$ $NR^{13}R^{14}$ wherein q and r are each independently an integer ranging from 0 to 3 except q and r are not both 0, —$(CH_2)_m(C_8$–$C_{10}$ aryl), or —$(CH_2)_m(5$–10 membered heteroaryl), wherein m is an integer ranging from 0 to 4, and wherein the foregoing $R^8$ groups, except H, are optionally substituted by 1 to 3 $R^{18}$ groups;

or where $R^6$ is as —$CH_2NR^8R^{15}$, $R^{15}$ and $R^8$ may be taken together to form a 4–10 membered monocyclic or polycyclic saturated ring or a 5–10 membered heteroaryl ring, wherein said saturated and heteroaryl rings optionally include 1 or 2 heteroatoms selected from O, S and —$N(R^8)$—, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{16}$ groups;

each $R^9$ and $R^{10}$ is independently H or $C_1$–$C_6$ alkyl;

each $R^{11}$, $R^{12}$, $R^{13}$ and $R^{14}$ is independently selected from H, $C_1$–$C_{10}$ alkyl, —$(CH_2)_m(C_8$–$C_{10}$ aryl), and —$(CH_2)_m$ (5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —$(CH_2)_p$ wherein p is an integer ranging from 0 to 3 such that a 4–7 membered saturated ring is formed that optionally includes 1 or 2 carbon-carbon double or triple bonds;

or $R^{13}$ and $R^{14}$ are taken together to form a 4–10 membered monocyclic or polycyclic saturated ring or a 5–10 membered heteroaryl ring, wherein said saturated and heteroaryl rings optionally include 1 or 2 heteroatoms selected from O, and —$N(R^8)$—, in addition to the nitrogen to which $R^{13}$ and $R^{14}$ are attached, said saturated ring optionally includes 1 or 2 carbon-carbon double or triple bonds, and said saturated and heteroaryl rings are optionally substituted by 1 to 3 $R^{16}$ groups;

$R^{15}$ is H, $C_1$–$C_{10}$ alkyl, $C_2$–$C_{10}$ alkenyl, or $C_2$–$C_{10}$ alkynyl, wherein the foregoing $R^{15}$ groups are optionally substituted by 1 to 3 substituents independently selected from halo and —$OR^9$;

each $R^{16}$ is independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)$ $NR^6R^7$, —$NR^6R^7$, hydroxy, $C_1$–$C_6$ alkyl, $C_1$–$C_6$ alkoxy, —$(CH_2)_m(C_6$–$C_{10}$ aryl), and —$(CH_2)_m(5$–10 membered heteroaryl), wherein m is an integer ranging from 0 to 4, and wherein said aryl and heteroaryl substituents are optionally substituted by 1 or 2 substituents independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)$ $NR^6R^7$, —$NR^6R^7$, hydroxy, $C_1$–$C_6$ alkyl, and $C_1$–$C_6$ alkoxy;

each $R^{17}$ is independently selected from H, $C_1$–$C_{10}$ alkyl, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4, provided that $R^8$ is not H where $R^{19}$ is —$CH_2S(O)_nR^9$;

$R^{18}$ is OH;

$R^{19}$ is $C_1$–$C_{10}$ alkyl, $C_2$–$C_{10}$ alkenyl, $C_2$–$C_{10}$ alkynyl, cyano, —$CH_2S(O)_nR^8$ wherein n is an integer ranging from 0 to 2, —$CH_2OR^8$, —$CH_2N(OR^9)R^8$, —$CH_2NR^8R^{15}$, —$(CH_2)_m(C_6$–$C_{10}$ aryl), or —$(CH_2)_m$ (5–10 membered heteroaryl), wherein m is an integer ranging from 0 to 4, and wherein the foregoing $R^{19}$ groups are optionally substituted by 1 to 3 $R^{15}$ groups;

or $R^{18}$ and $R^{19}$ are taken together to form an oxazolyl ring as shown below

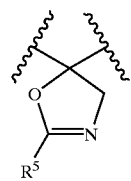

and;

each $R^{21}$ and $R^{22}$ is independently H, hydroxy, $C_1$–$C_8$ alkoxy, $C_1$–$C_6$ alkyl, $C_2$–$C_6$ alkenyl, $(CH_2)_m(C_6$–$C_{10})$ aryl, $(CH_2)_m$(5–10 membered heteroaryl), wherein m is an integer ranging from 0 to 4, or $C_2$–$C_{10}$ alkylyl.

* * * * *